(12) United States Patent
Pellicciari

(10) Patent No.: US 8,999,964 B2
(45) Date of Patent: Apr. 7, 2015

(54) TGR5 MODULATORS AND METHODS OF USE THEREOF

(75) Inventor: Roberto Pellicciari, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 314 days.

(21) Appl. No.: 13/129,947

(22) PCT Filed: Nov. 19, 2009

(86) PCT No.: PCT/US2009/065199
§ 371 (c)(1),
(2), (4) Date: Jul. 18, 2011

(87) PCT Pub. No.: WO2010/059859
PCT Pub. Date: May 27, 2010

(65) Prior Publication Data
US 2011/0263555 A1    Oct. 27, 2011

(30) Foreign Application Priority Data

Nov. 19, 2008    (EP) ..................................... 08169460

(51) Int. Cl.
*A61K 31/575*    (2006.01)
*C07J 9/00*    (2006.01)
(52) U.S. Cl.
CPC ...................................... *C07J 9/005* (2013.01)
(58) Field of Classification Search
USPC .......................................... 552/551; 514/182
See application file for complete search history.

(56) References Cited

U.S. PATENT DOCUMENTS 5,763,433 A    6/1998 Morfin

FOREIGN PATENT DOCUMENTS

| WO | WO 94/08588 A1 | 4/1994 |
| WO | WO 2004/067008 A1 | 8/2004 |
| WO | WO 2008/091540 A3 | 7/2008 |

OTHER PUBLICATIONS

Hagey et al., "A Novel Primary Bile Acid in the Shoebill Stork and Herons and its Phylogenetic Significance", *Journal of Lipid Research*, 43:685-690 (2002).
Iida et al., "Potential Bile Acid Metabolites. 25. Synthesis and Chemical Properties of Stereoisomeric 3α, 7α, 16-and 3 α, 7α, 15-Trihydroxy-5β-cholan-24-oic Acids", *Chem. Pharm. Bull.*, 50:1327-1334 (2002).
Nonappa et al., "First Chemical Synthesis, Aggregation Behavior and Cholesterol Solubilization Properties of Pythocholic Acid and 16α-Hydroxycholic Acid", *Eur. J. Org. Chem.*, 3331-3336 (2007).
Yasukawa et al., "Relative Inhibitory Activity of Bile Acids Against 12-O-tetradecanoylphorbol-13-acetate-induced inflammation, and chenodeoxycholic Acid Inhibition of Tumour Promotion in Mouse Skin Two-Stage Carcinogenesis", *Journal of Pharmacy and Pharmacology*, 61:1051-1066 (2009).
Pellicciari et al. "Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5." *J. Med. Chem.* 50(2007):4265-4268.
Katona, B.W. et al., "Synthesis, Characterization, and Receptor Interaction Profiles of Enantiomeric Bile Acids", *J. Med. Chem.*, 50(24):6048-6058 (2007).
Katsuma, S. et al., "Bile acids promote glucagon-like peptide-1 secretion through TGR5 in a murine enteroendocrine cell line STC-1". *Biochem. Biophys. Res. Commun.* 329:386-390 (2005).
Kawamata, Y. et al., "A G protein-coupled receptor responsive to bile acids", *J. Biol. Chem.* 278 (11): 9435-9440 (2003).
Maruyama, T. et al., "Targeted disruption of G protein-coupled bile acid receptor 1 (Gpbar1/M-Bar) in mice" *J. Endocrinol.* 191:197-205 (2006).
Patani, G.A. et al., "Bioisosterism: a Rational Approach in Drug Design", *Chem. Rev.*, 96:3147-3176 (1996).
Sato, H. et al., "Anti-hyperglycemic activity of a TGR5 agonist isolated from *Olea europaea*", *Biochem. and Biophys. Res. Commun.*, 362(4):793-798 (2007).
Takeda, S. et al., "Identification of G protein-coupled receptor genes from the human genome sequence", *FEBS Lett.* 520: 97-101 (2002).
Watanabe, M. et al., "Bile acids induce energy expenditure by promoting intracellular thyroid hormone activation", *Nature.* 439,484-489 (2006).

*Primary Examiner* — Barbara P Badio
(74) *Attorney, Agent, or Firm* — Cooley LLP; Ivor R. Elrifi; Heidi A. Erlacher

(57) ABSTRACT

The invention relates to compounds of Formula (A): (A) or a salt, solvate, hydrate, or amino acid conjugate thereof. The compounds of formula A are TGR5 modulators useful for the prevention and treatment of disease.

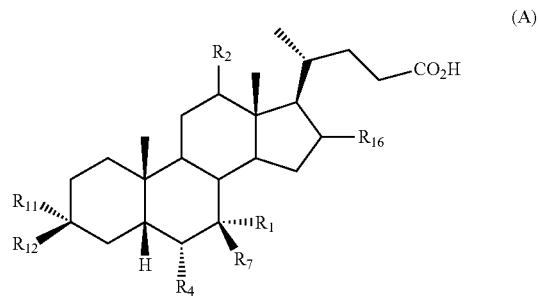

17 Claims, 9 Drawing Sheets

LCA EC$_{50}$ = 64.5 μM
(95% CI = 20.8-200 μM)
R$^2$ = 0.92

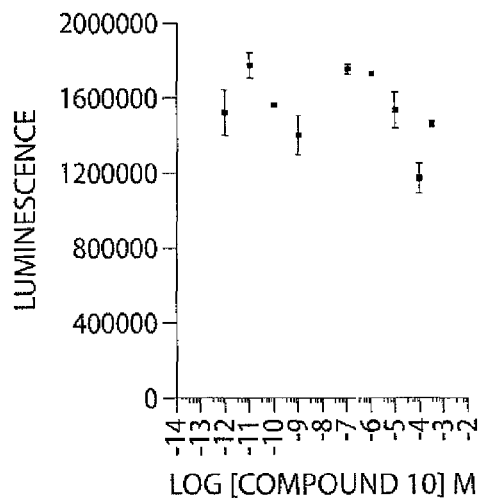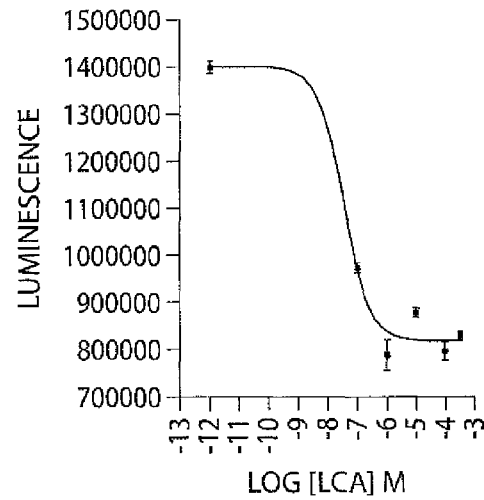
Fig. 5A
Fig. 5B
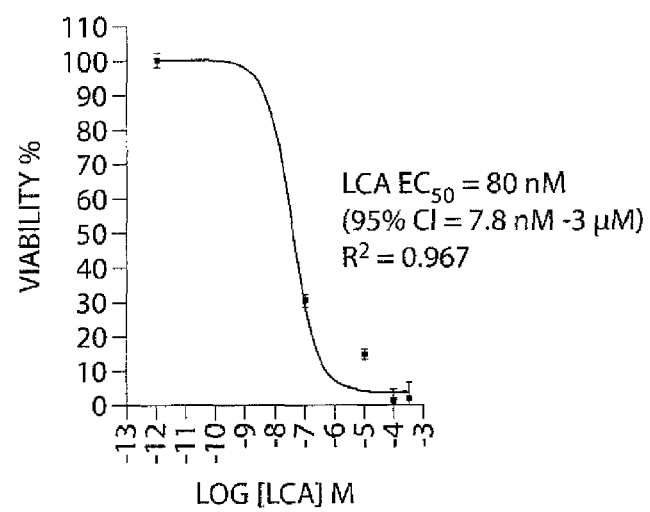
Fig. 5C

TGR5 MODULATORS AND METHODS OF USE THEREOF

RELATED APPLICATIONS

This application is a 35 U.S.C. §371 National Phase Application of PCT/US2009/065199, filed Nov. 19, 2009, which claims priority to European Application No. 08169460.6, filed Nov. 19, 2008, the contents of which are incorporated herein.

FIELD OF THE INVENTION

The invention concerns relates to compounds that modulate TGR5 and compositions containing such compounds useful in methods for the treatment and prevention of disease. Specifically, the compounds of the invention are analogues of chenodeoxycholic acid having a substituent at the C-16 position.

BACKGROUND OF THE INVENTION

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm. Kawamata et al. 2003, J. Bio. Chem., 278, 9435. TGR5 has been found to be identical to hGPCR19 reported by Takeda et al. 2002, FEBS Lett. 520, 97-101.

TGR5 is associated with the intracellular accumulation of cAMP, that is widely expressed in diverse cell types. While the activation of this membrane receptor in macrophages decreases pro-inflammatory cytokine production, (Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G protein-coupled receptor responsive to bile acids. J. Biol. Chem. 2003, 278, 9435-9440) the stimulation of TGR5 by BAs in adipocytes and myocytes enhances energy expenditure (Watanabe, M.; Houten, S. M.; Mataki, C.; Christoffolete, M. A.; Kim, B. W.; Sato, H.; Messaddeq, N.; Harney, J. W.; Ezaki, O.; Kodama, T.; Schoonjans, K.; Bianco, A. C.; Auwerx, J., Bile acids induce energy expenditure by promoting intracellular thyroid hormone activation. *Nature*. 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T.; Tanaka, K.; Suzuki, J.; Miyoshi, H.; Harada, N.; Nakamura, T.; Miyamoto, Y.; Kanatani, A.; Tamai, Y., Targeted disruption of G protein-coupled bile acid receptor 1 (Gpbar1/MBar) in mice. *J. Endocrinol.* 2006, 191, 197-205). In addition and in line with the involvement of TGR5 in energy homeostasis, bile acid activation of the membrane receptor has also been reported to promote the production of glucagon-like peptide 1 (GLP-1) in murine enteroendocrine cell lines (Katsuma, S.; Hirasawa, A.; Tsujimoto, G., Bile acids promote glucagon-like peptide-1 secretion through TGR5 in a murine enteroendocrine cell line STC-1. Biochem. Biophys. Res. Commun. 2005, 329, 386-390). On the basis of all the above observations, TGR5 is an attractive target for the treatment of metabolic diseases e.g., obesity, diabetes (type I and type II), dyslipidemia, non-alcoholic steatohepatitis (NASH), and the metabolic syndrome.

Few examples of TGR5 agonists have been so far described in literature. Recently, 23-alkyl-substituted and 6,23-alkyl-disubstituted derivatives of chenodeoxycholic acid, such as the 6α-ethyl-23(S)-methyl-chenodeoxycholic acid shown below, have been reported as potent and selective agonists of TGR5 (Pellicciari, R.; Sato, H.; Gioiello, A.; Costantino, G.; Macchiarulo, A.; Sadeghpour, B. M.; Giorgi, G.; Schoonjans, K.; Auwerx, J., Nongenomic actions of bile acids. Synthesis and preliminary characterization of 23- and 6,23-alkyl-substituted bile acid derivatives as selective modulators for the g-protein coupled receptor TGR5. *J. Med. Chem.* 2007, 50, 4265-4268).

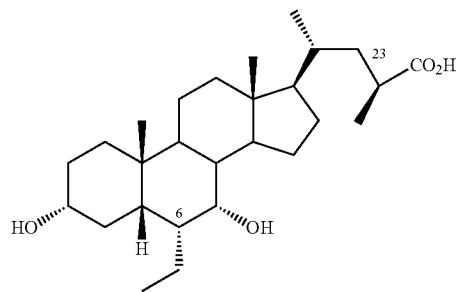 [SMILES: CC[C@H]1[C@@H](O)C2C3CC[C@H]([C@H](C)C[C@H](C)C(=O)O)[C@@]3(C)CCC2[C@@]2(C)CC[C@@H](O)C[C@@H]12]

In particular, methylation at the $C_{23}$—(S) position of natural BAs confers a marked selectivity to TGR5 over FXR (farnesoid X receptor) activation, whereas the 6α-alkyl substitution increases the potency at both receptors. Other TGR5 agonists include 6-methyl-2-oxo-4-thiophen-2-yl-1,2,3,4-tetrahydro-pyrimidine-5-carboxylic acid benzyl ester (WO004067008, Takeda Chemical Industries LTD, Japan, 2004) and oleanoic acid (Sato, H.; Genet, C.; Strehle, A.; Thomas, C.; Lobstein, A.; Wagner, A.; Mioskowski, C.; Auwerx, J.; Saladin, R., Anti-hyperglycemic activity of a TGR5 agonist isolated from *Olea europaea*. *Biochem. and Biophys. Res. Commun.* 2007, 362, 793-798; Ito, F.; Hinuma, K.; Kanzaki, N.; Mild, T.; Kawamata, Y.; Oi, S.; Tawaeaishi, T.; Ishichi, Y.; Hirohashi, M. Preparation of aromatic ring-fused cyclic compounds as TGR5 receptor agonists. PN: WO2004067008, 2004. More recently, the first synthesis of enantiomeric chenodeoxycholic acid (CDCA) and lithocholic acid (LCA) has allowed to assess the specificity of the interaction of natural BAs to TGR5 (Katona, B. W.; Cummins, C. L.; Ferguson, A. D.; Li, T.; Schmidt, D. R.; Mangelsdorf, D. J.; Covey, D. F., Synthesis, Characterization, and Receptor Interaction Profiles of Enantiomeric Bile Acids. *J. Med. Chem.* 2007, 50, 6048-6058).

While these chemical tools have provided for the first time a pharmacological differentiation of genomic versus nongenomic effects of BAs, some of them also allowed to draw a first structure-activity relationship study where the presence of an accessory binding pocket in TGR5 plays a pivotal role in determining ligand selectivity (Pellicciari, R.; Sato, H.; Gioiello, A.; Costantino, G.; Macchiarulo, A.; Sadeghpour, B. M.; Giorgi, G.; Schoonjans, K.; Auwerx, J., Nongenomic actions of bile acids. Synthesis and preliminary characterization of 23- and 6,23-alkyl-substituted bile acid derivatives as selective modulators for the g-protein coupled receptor TGR5. *J. Med. Chem.* 2007, 50, 4265-4268). In this context, the availability of more potent and selective TGR5 modulators is necessary to further identify additional features affecting receptor activation and characterize the physiological and pharmacological actions of this receptor.

There is a need for the development of TGR5 modulators for the treatment and prevention of disease. The present invention has identified compounds that are chenodeoxycholic acid analogues which have a substituent at the C-16 position as well as methods of using these compounds to treat disease.

SUMMARY OF THE INVENTION

The present invention relates to compounds and their use to treat and prevent diseases that involve modulation of the TGR5 receptor, such as metabolic disease, inflammatory disease, liver disease, autoimmune disease, cardiac disease, kidney disease, cancer, and gastrointestinal disease. Specifically, the compounds of the invention are analogues of chenodeoxycholic acid that are substituted at the C-16 position of the D ring as shown below.

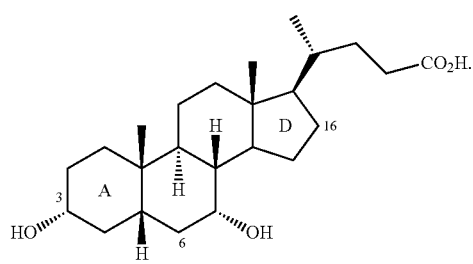

In one aspect, the invention includes a compound having the formula A:

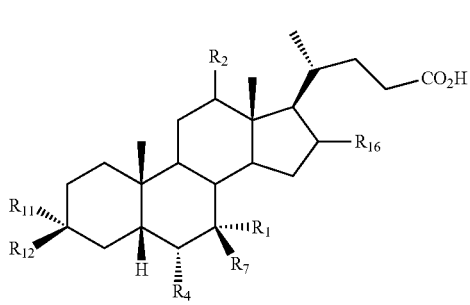

(A)

or a salt, solvate, hydrate, or amino acid conjugate, wherein:
$R_1$ is hydrogen, hydroxy, substituted or unsubstituted alkyl, or halogen;
$R_2$ is hydrogen or hydroxy; $R_4$ is hydrogen, substituted or unsubstituted alkyl, or halogen;
$R_7$ is hydrogen, substituted or unsubstituted alkyl, or hydroxy;
$R_{11}$ is hydroxyl, $OSO_3H$, $OSO_3^-$, $OCOCH_3$, $OPO_3H$, $OPO_3^{2-}$, $OC_6H_8O_6^-$, or hydrogen;
$R_{12}$ is hydroxyl, $OSO_3H$, $OSO_3^-$, $OCOCH_3$, $OPO_3H$, $OPO_3^{2-}$, $OC_6H_8O_6^-$, or hydrogen, or taken together $R_{11}$ and $R_{12}$ form a carbonyl; and $R_{16}$ is hydroxyl, alkoxy, and halogen, provided that when $R_2$, $R_4$, $R_7$, and $R_{12}$ are hydrogen,
$R_1$ and $R_{11}$ are OH, then $R_{16}$ is not alpha OH.

In another aspect, the invention includes a compound having the formula B:

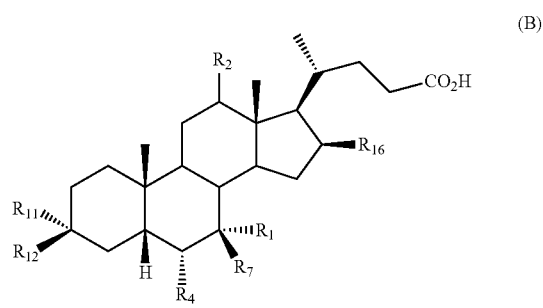

(B)

or a salt, solvate, hydrate, or amino acid conjugate thereof, wherein $R_1$, $R_2$, $R_4$, $R_7$, $R_{11}$, $R_{12}$, and $R_{16}$ are as described herein.

In another aspect, the invention includes a compound having the formula C:

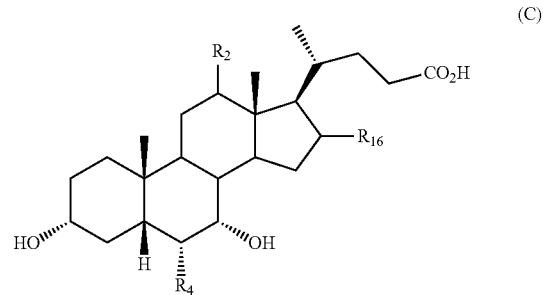

(C)

or a salt, solvate, hydrate, or amino acid conjugate thereof, wherein $R_2$, $R_4$, and $R_{16}$ are as described herein.

In another aspect, the invention includes a compound having the formula D:

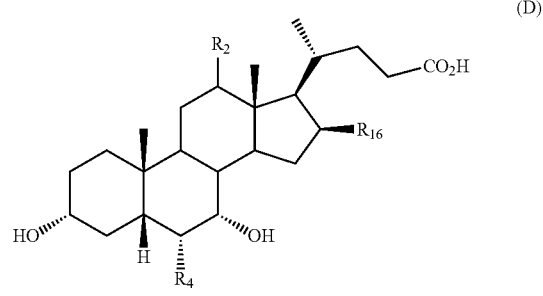

(D)

or a salt, solvate, hydrate, or amino acid conjugate thereof, wherein $R_2$, $R_4$, and $R_{16}$ are as described herein.

In another aspect, the invention includes a compound having the formula E:

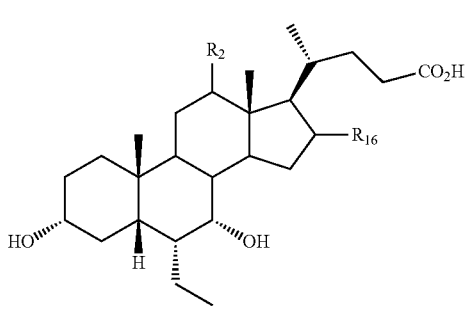

(E)

or a salt, solvate, hydrate, or amino acid conjugate thereof, wherein $R_2$ and $R_{16}$ are as described herein.

In another aspect, the invention includes a compound having the formula F:

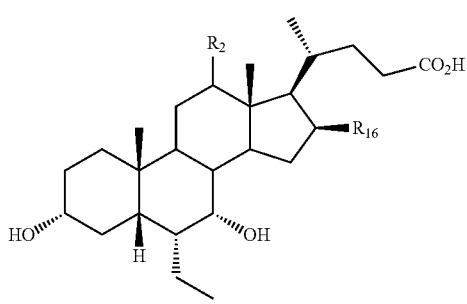

(F)

or a salt, solvate, hydrate, or amino acid conjugate thereof, wherein $R_2$ and $R_{16}$ are as described in claim 1.

The invention includes a compound or a salt, solvate, hydrate, or amino acid conjugate thereof, wherein $R_1$ is OH. The invention includes a compound or a salt, solvate, hydrate, or amino acid conjugate thereof, wherein $R_7$ is H. The invention includes a compound or a salt, solvate, hydrate or amino acid conjugate thereof, wherein $R_2$ is H. The invention includes a compound or a salt, solvate, hydrate or amino acid conjugate thereof, wherein $R_2$ is alpha-OH. The invention includes a compound or a salt, solvate, hydrate or amino acid conjugate thereof, wherein $R_2$ is beta-OH. The invention includes a compound or a salt, solvate, hydrate or amino acid conjugate thereof, wherein $R_4$ is unsubstituted alkyl. The invention includes a compound or a salt, solvate, hydrate or amino acid conjugate thereof, wherein $R_4$ is ethyl. The invention includes a compound or a salt, solvate, hydrate, or amino acid conjugate thereof, wherein $R_{11}$ is hydroxyl. The invention includes a compound or a salt, solvate, hydrate, or amino acid conjugate thereof, wherein $R_{12}$ is hydrogen. The invention includes a compound or a salt, solvate, hydrate, or amino acid conjugate thereof, wherein $R_{16}$ is alpha hydroxyl. The invention includes a compound or salt, solvate, hydrate, or amino acid conjugate thereof, wherein $R_{16}$ is beta hydroxyl.

The invention includes a compound, wherein the compound is Compound 10:

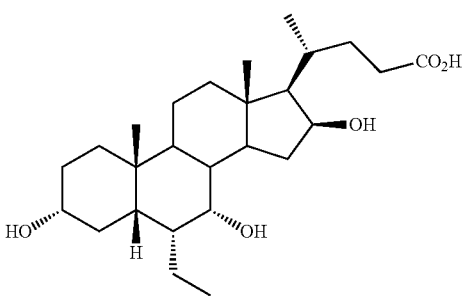

(10)

or a salt, solvate, hydrate, or amino acid conjugate thereof. The invention includes a compound, wherein the compound is a pharmaceutically acceptable salt.

The invention includes a composition comprising a compound of the invention and at least one pharmaceutically acceptable excipient. The invention includes a compound or composition for use in a method of treating or preventing a disease, the method comprising administering the compound of the invention. The invention includes the use of a compound of the invention in the manufacture of a medicament for a method of treating or preventing disease.

The invention includes the use of a compound having the formula A:

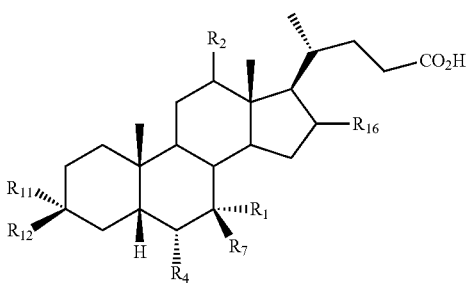

(A)

or a salt, solvate, hydrate, or amino acid conjugate thereof, wherein: $R_1$ is hydrogen, hydroxy, substituted or unsubstituted alkyl, or halogen;

$R_2$ is hydrogen or hydroxy; $R_4$ is hydrogen, substituted or unsubstituted alkyl, or halogen;

$R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$, $OC_6H_8O_6^-$, or hydrogen; $R_{12}$ is hydroxyl, $OSO_3H$, $OSO_3^-$, $OCOCH_3$, $OPO_3H$, $OPO_3^{2-}$, $OC_6H_8O_6^-$, or hydrogen, or taken together $R_{11}$ and $R_{12}$ form a carbonyl; and $R_{16}$ is hydroxyl, alkoxy, and halogen, provided that when $R_2$, $R_4$, $R_7$, and $R_{12}$ are hydrogen, $R_1$ and $R_{11}$ are OH, then $R_{16}$ is not alpha OH in the manufacture of a medicament for treating or preventing disease. The invention includes a method of treating disease by administering to a subject a compound having the formula A or a salt, solvate, hydrate, or amino acid conjugate thereof.

The invention includes the use, wherein the disease is selected from metabolic disease, inflammatory disease, liver disease, autoimmune disease, cardiac disease, kidney disease, cancer, and gastrointestinal disease. The invention includes the use, wherein the compound or composition is administered to the subject orally, parentally, intravenously, or topically. The invention includes the use, wherein the subject is a human.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DESCRIPTION OF THE FIGURES

FIG. 5 is a series of 3 graphs (A-C) that shows the results for compound 10 of in vitro cytotoxicity testing measuring ATP-release after 4 hours of stimulation using hepatic (HepG2) cell lines. LCA is a positive control.

DESCRIPTION OF THE INVENTION

Figure 1:
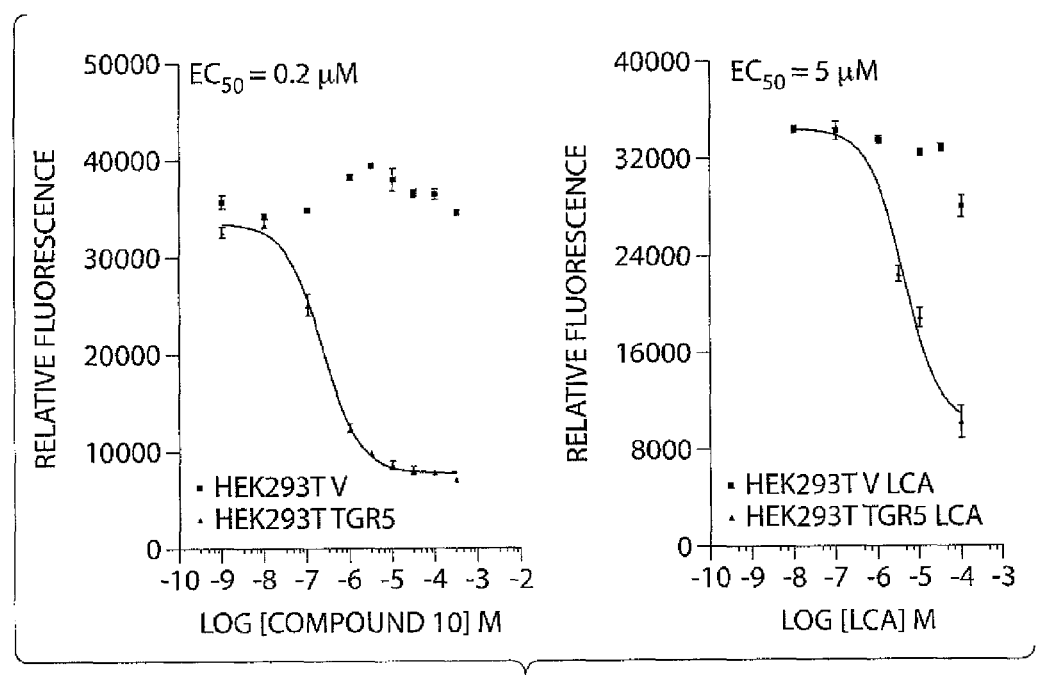
FIG. 1 is a series of 2 graphs (A-B) that shows the results of FRET assay using compound 10 (FIG. 1A) and LCA (FIG. 1B) on HEK293T cells transiently transfected with vector alone (V) or TGR5 expressing vector (TGR5).
Figure 2A:
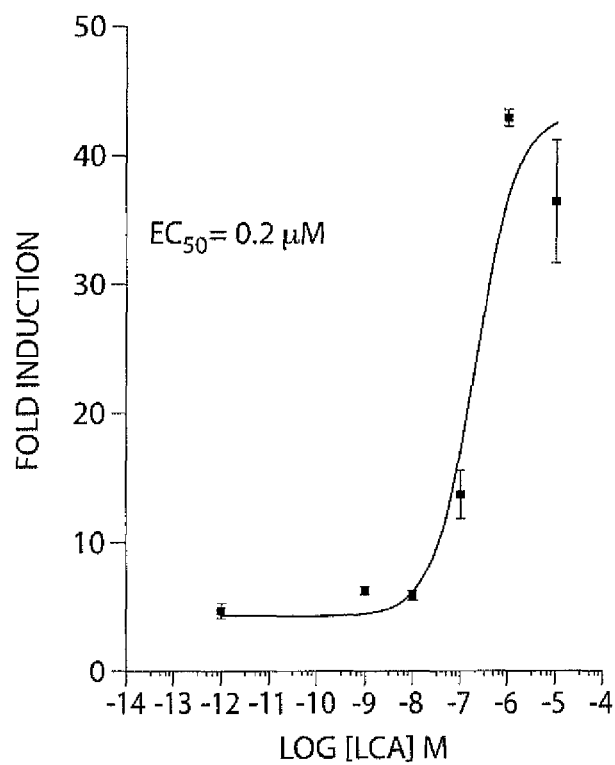
FIG. 2 is a series of 2 graphs (A-B) that show transactivation assay (CRE-Luc reporter) results for compound 10 and LCA (positive control) using TGR5 expressing HEK293T cells.
Figure 2B:
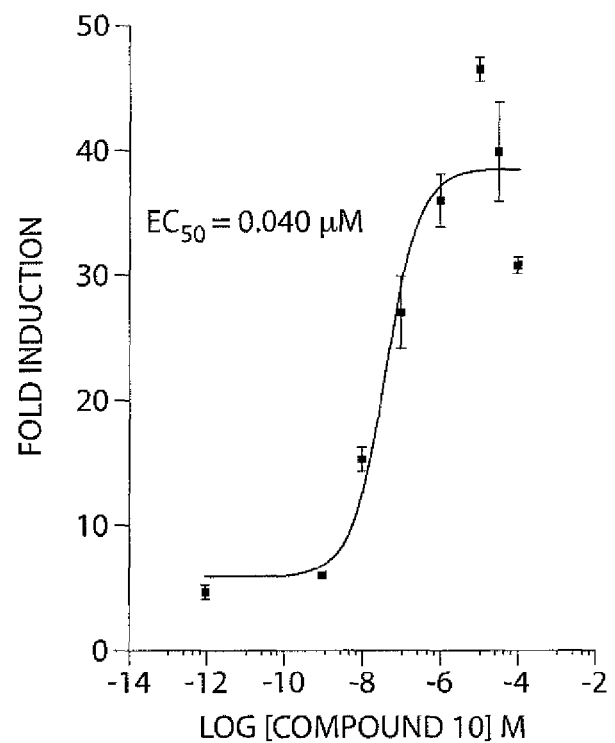

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

In one aspect, the invention includes a compound of formula A:

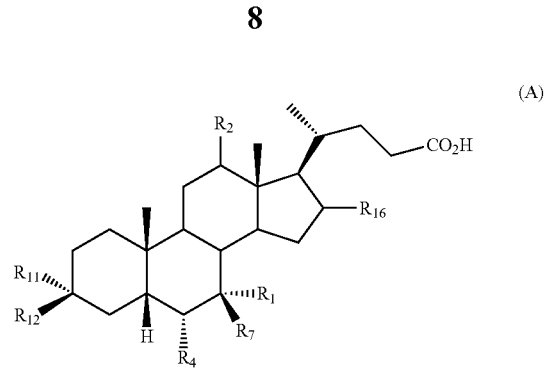

(A)

or a salt, solvate, hydrate, or amino acid conjugate, wherein, $R_1$ is hydrogen, hydroxy, substituted or unsubstituted alkyl, or halogen;

$R_2$ is hydrogen or hydroxyl; $R_4$ is hydrogen, substituted or unsubstituted alkyl, or halogen; $R_7$ is hydrogen, substituted or unsubstituted alkyl, or hydroxyl; $R_{11}$ is hydroxyl, $OSO_3H$, $OSO_3^-$, $OCOCH_3$, $OPO_3H$, $OPO_3^{2-}$, $OC_6H_8O_6^-$, or hydrogen; $R_{12}$ is hydroxyl, $OSO_3H$, $OSO_3^-$, $OCOCH_3$, $OPO_3H$, $OPO_3^{2-}$, $OC_6H_8O_6^-$, or hydrogen, or taken together $R_{11}$ and $R_{12}$ form a carbonyl; $R_{16}$ is hydroxyl, alkoxy, or halogen. In one aspect, the invention does not include a compound wherein $R_2$, $R_4$, $R_7$, and $R_{12}$ are hydrogen, $R_1$ and $R_{11}$ are OH, and $R_{16}$ is alpha OH. In another aspect, the invention provides a compound of formula A or a salt, solvate, hydrate, or amino acid conjugate, provided that when $R_2$, $R_4$, $R_7$, and $R_{12}$ are hydrogen and $R_1$ and $R_{11}$ are OH, then $R_{16}$ is not alpha OH. In another aspect, the invention does not include the compound:

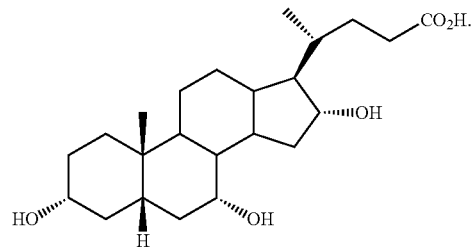 [SMILES: C[C@H](CCC(=O)O)[C@@H]1C2CCC3C(C2C[C@H]1O)[C@H](O)C[C@@H]1C[C@H](O)CC[C@]31C]

In one aspect, the invention includes a compound having the formula B:

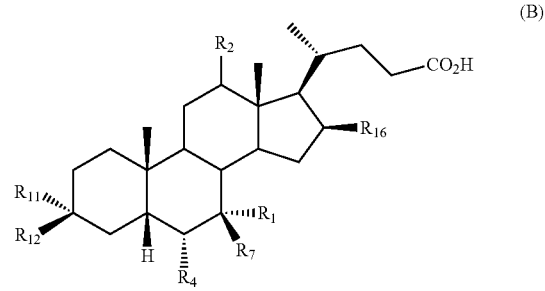

(B)

or a salt, solvate, hydrate, or amino acid conjugate thereof, wherein $R_1$, $R_2$, $R_4$, $R_7$, $R_{11}$, $R_{12}$, and $R_{16}$ are as above.

In one aspect, the invention includes a compound having the formula C:

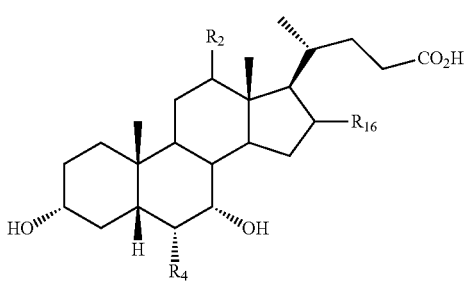

(C)

or a salt, solvate, hydrate, or amino acid conjugate thereof, wherein $R_2$, $R_4$, and $R_{16}$ are as described above.

In one aspect, the invention includes a compound having the formula D:

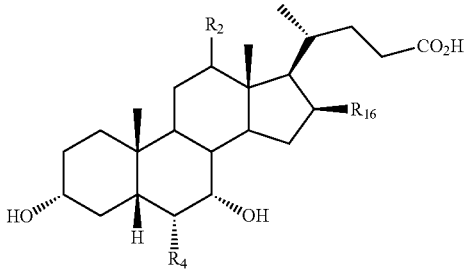

(D)

or a salt, solvate, hydrate, or amino acid conjugate thereof, wherein $R_2$, $R_4$, and $R_{16}$ are as described above.

In one aspect, the invention includes a compound having the formula E:

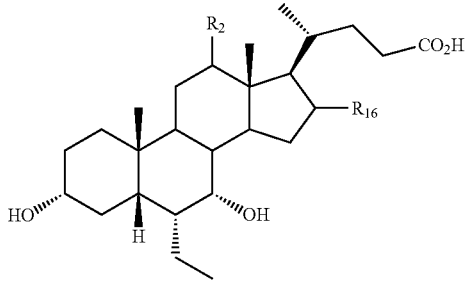

(E)

or a salt, solvate, hydrate, or amino acid conjugate thereof, wherein $R_2$ and $R_{16}$ are as described above.

In one aspect, the invention includes a compound having the formula F:

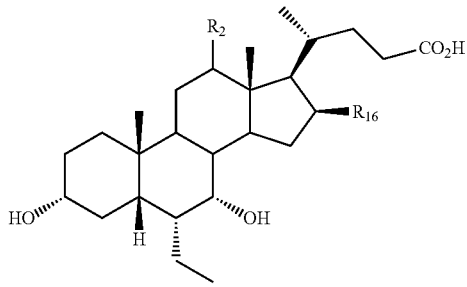

(F)

or a salt, solvate, hydrate, or amino acid conjugate thereof, wherein $R_2$ and $R_{16}$ are as described above.

In one aspect, the invention includes a compound or a salt, solvate, hydrate, or amino acid conjugate thereof, wherein $R_1$ is OH. In one aspect, the invention includes a compound or a salt, solvate, hydrate, or amino acid conjugate thereof, wherein $R_7$ is H. In one aspect, the invention includes a compound of a salt, solvate, hydrate, or amino acid conjugate thereof, wherein $R_1$ is OH and $R_7$ is H.

In one aspect, the invention includes a compound or a salt, solvate, hydrate or amino acid conjugate thereof, wherein $R_2$ is H. In one aspect, the invention includes a compound or a salt, solvate, hydrate or amino acid conjugate thereof, wherein $R_2$ is alpha-OH. In one aspect, the invention includes a compound or a salt, solvate, hydrate or amino acid conjugate thereof, wherein $R_2$ is beta-OH.

In one aspect, the invention includes a compound or a salt, solvate, hydrate or amino acid conjugate thereof, wherein $R_4$ is unsubstituted alkyl. In one aspect, the invention includes a compound or a salt, solvate, hydrate or amino acid conjugate thereof, wherein $R_4$ is ethyl.

In one aspect, the invention includes r a compound or a salt, solvate, hydrate, or amino acid conjugate thereof, wherein $R_{11}$ is hydroxyl. In one aspect, the invention includes a compound or a salt, solvate, hydrate, or amino acid conjugate thereof, wherein $R_{12}$ is hydrogen.

In one aspect, the invention includes the compound 10:

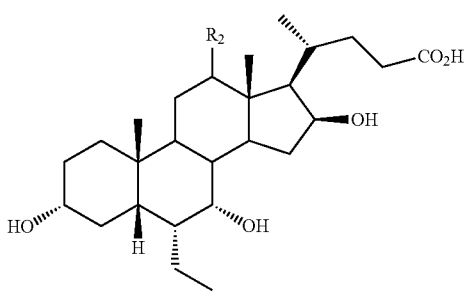

(10)

or a salt, solvate, hydrate, or amino acid conjugate thereof.

In one aspect, the invention includes a compound, wherein the compound is a pharmaceutically acceptable salt.

In one aspect, the invention includes a composition comprising a compound or a salt, solvate, hydrate, or amino acid conjugate thereof and at least one excipient. In one aspect, the invention includes a composition comprising a compound or a salt, solvate, hydrate, or amino acid conjugate thereof and at least one pharmaceutically acceptable excipient.

In one aspect, the invention includes the use of a compound or a composition of the invention, in the manufacture of a medicament for treating or preventing disease in a subject. In another aspect, the invention includes a method of treating or preventing disease in a subject by administering a compound or a composition of the invention. In one aspect, the invention includes a therapeutically effective amount of a compound or composition of the invention is administered to the subject. In one aspect, the invention includes a prophylactically effective amount of a compound or composition of the invention is administered.

In one aspect, the invention includes the use of the compound or composition of the invention, in the manufacture of a medicament for a treating or preventing a disease in a subject that involves modulation of the TGR5 receptor. The invention includes a method of treating or preventing a disease that involves modulation of the TGR5 receptor in a subject by administering a compound or composition of the invention.

In one aspect, the invention includes the use, wherein the disease is selected from metabolic disease, inflammatory disease, liver disease, autoimmune disease, cardiac disease, kidney disease, cancer, and gastrointestinal disease. The invention includes a method of treating or preventing a disease selected from metabolic disease, inflammatory disease, liver disease, autoimmune disease, cardiac disease, kidney disease, cancer, and gastrointestinal disease.

In one aspect, the invention includes the use, wherein the disease is a metabolic disease selected from obesity, diabetes, metabolic syndrome, insulin resistance, hypertension, and dyslipidemia. The invention includes a method of treating or preventing a metabolic disease selected from obesity, diabetes, diabesity, metabolic syndrome, insulin resistance, prediabetic insulin resistance, hypertension, and dyslipidemia.

In one aspect, the invention includes the use, wherein the disease is an inflammatory disease selected from allergy, osteoarthritis, appendicitis, bronchial asthma, pancreatitis, allergic rash, and psoriasis. The invention includes a method of treating or preventing an inflammatory disease selected from allergy, osteoarthritis, appendicitis, bronchial asthma, pancreatitis, allergic rash, and psoriasis.

In one aspect, the invention includes the use, wherein the disease is an autoimmune disease selected from rheumatoid arthritis, multiple sclerosis, and type I diabetes. The invention includes a method of treating or preventing an autoimmune disease selected from rheumatoid arthritis, multiple sclerosis, and type I diabetes.

In one aspect, the invention includes the use, wherein the disease is a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth. The invention includes a method of treating or preventing a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention includes the use, wherein the disease is kidney disease selected from diabetic nephropathy, chronic renal failure, hypertensive nephrosclerosis, chronic glomerulonephritis, chronic transplant glomerulopathy, chronic interstitial nephritis, and polysystic kidney disease. The invention includes a method of treating or preventing kidney disease selected from diabetic nephropathy, chronic renal failure, hypertensive nephrosclerosis, chronic glomerulonephritis, chronic transplant glomerulopathy, chronic interstitial nephritis, and polysystic kidney disease.

In one aspect, the invention includes the use, wherein the disease is cancer selected from colorectal cancer, liver cancer, heptacellular carcinoma, cholangio carcinoma, renal cancer, gastric cancer, pancreatic cancer, prostate cancer, and insulanoma. The invention includes a method of treating or preventing cancer selected from colorectal cancer, liver cancer, heptacellular carcinoma, cholangio carcinoma, renal cancer, gastric cancer, pancreatic cancer, prostate cancer, and insulanoma.

In one aspect, the invention includes the use, wherein the disease is a liver disease selected from nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, α1-antitrypsin deficiency, total parenteral nutrition (TPN), cholelithiasis, TPN-associated cholestasis and sepsis. The invention includes a method of treating or preventing a liver disease selected from nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, a1-antitrypsin deficiency, total parenteral nutrition (TPN), cholelithiasis, TPN-associated cholestasis and sepsis.

In one aspect, the invention includes the use, wherein the cardiac disease is selected from congestive heart failure, myocardial infarction, atherosclerosis, angina pectoris, arteriosclerosis and cerebrovascular disease (hemorrhage, stroke, cerebrovascular infarction). The invention includes a method of treating or preventing a cardiac disease selected from congestive heart failure, myocardial infarction, atherosclerosis, angina pectoris, arteriosclerosis and cerebrovascular disease (hemorrhage, stroke, cerebrovascular infarction).

In one aspect, the invention includes a disease involving modulation of the TGR5 receptor. In one aspect, the invention includes a compound that is a TGR5 agonist. In one aspect, the compound is a selective TGR5 agonist over FXR activator.

In one aspect, the compound or composition of the invention is administered to the subject orally, parentally, intravenously, or topically. In one aspect, the subject is a human.

DEFINITIONS

For convenience, certain terms used in the specification, examples and appended claims are collected here.

The term "treating", as used herein, means relieving, lessening, reducing, eliminating, modulating, or ameliorating, i.e. causing regression of the disease state or condition.

The term "preventing", as used herein means, to completely or almost completely stop a disease state or condition, from occurring in a patient or subject, especially when the patient or subject is predisposed to such or at risk of contracting a disease state or condition. Preventing can also include inhibiting, i.e. arresting the development, of a disease state or condition, and relieving or ameliorating, i.e. causing regression of the disease state or condition, for example when the disease state or condition may already be present.

As used herein, the term "amino acid conjugates" refers to conjugates of the compounds of the formulae of the invention with any suitable amino acid. Such suitable amino acid conjugates of the compounds of the formulae of the invention will have the added advantage of enhanced integrity in bile or intestinal fluids. Suitable amino acids include but are not limited to glycine and taurine. Thus, the present invention encompasses the glycine and taurine conjugates of any of the compounds of the invention.

As used herein, "BA" means bile acid and bile acid derivatives. Bile acids are steroid carboxylic acids derived from cholesterol. The primary bile acids are cholic and chenodeoxycholic acids. In the body, these acids are conjugated with glycine or taurine before they are secreted into the bile.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain, $C_3$-$C_6$ for branched chain). In some examples, a straight chain or branched chain alkyl has four or fewer carbon atoms in its backbone. Further, cycloalkyls have from three to eight carbon atoms in their ring structure.

The term "substituted alkyl" refers to an alkyl moieties having a substituent replace one or more hydrogen atoms on at least one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

Unless the number of carbons is otherwise specified, "lower alkyl" includes an alkyl group, as defined above, but having from one to ten, for example, from one to six, carbon atoms in its backbone structure.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). Another anionic group is a carboxylate.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Stable compound" and "stable structure" are meant to indicate a compound that is sufficiently robust to survive isolation to a useful degree of purity from a reaction mixture, and formulation into an efficacious therapeutic agent.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

As defined herein, the term "derivative", e.g., in the term "bile acid derivatives", refers to compounds that have a common core 4-membered ring structure, and are substituted with various groups as described herein.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

"Combination therapy" (or "co-therapy") includes the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

A "therapeutically effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight and tolerance to drugs.

The term "reducing the risk of", as used herein, means to lower the likelihood or probability of a central nervous system disease, inflammatory disease and/or metabolic disease from occurring in a patient, especially when the patient or subject is predisposed to such occurrence.

A "salt" of a compound of the invention is a product of the compound that contains an ionic bond and its typically produced by reacting the compound with either an acid or a base.

A "pharmaceutically acceptable salt" is a salt suitable for administering to a subject.

A "composition" is a formulation containing a compound of the invention in a form suitable for administration to a subject. In another embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

Compounds of the invention also include prodrugs or physiologically equivalent derivatives. A "prodrug" or "physiologically equivalent derivative" includes a precursor form of the drug which is metabolically converted in vivo to produce the active drug. The invention further contemplates the use of prodrugs which are converted in vivo to the TGR5 modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the TGR5 modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate TGR5 modulating compound which subsequently decomposes to yield the active TGR5 modulating compound. In one embodiment, the prodrug is a reduced form of a carboxylate, sulfate or sulfonate, e.g., an alcohol or thiol, which is oxidized in vivo to the TGR5 modulating compound. Furthermore, an anionic moiety can be esterified to a group which is actively transported in vivo, or which is selectively taken up by target organs.

The term "TGR5 modulator" means any compound that interacts with the TGR5 receptor. The interaction is not limited to a compound acting as an antagonist, agonist, partial agonist, or inverse agonist of the TGR5 receptor. In one aspect, the compounds of the present invention act as an antagonist of the TGR5 receptor. In another aspect, the compounds of the present invention act as an agonist of the TGR5 receptor. In another aspect, the compounds of the present invention act as a partial agonist of the TGR5 receptor. In another aspect, the compounds of the present invention act as an inverse agonist of the TGR5 receptor. The profile of a ligand, traditionally, endogenous or synthetic, is characterized by its intrinsic efficacy 'e' originally described by Furchgott in 1966. It is used to express the degree to which the different ligands produce varying biological responses while occupying the same number of receptors. Generally, the term "agonist" means a compound that enhances the activity of another molecule or receptor site. An agonist, by classical definition, whether a orthosteric, allosteric, inverse or a co-agonist has a property to bind to the receptor, alter its receptor state and result in a biological action. Consequently, agonism is defined as a property of an agonist or a ligand to produce a biological action. In contrast to this, an "antagonist" is essentially an agonist with high affinity to the same receptor macromolecule, but with very less or negligible intrinsic efficacy, and thus sterically prevents the biological actions of an agonist. As a property, antagonism may be functional or physiological, where an agonist has a direct competition for the receptor site in former and opposing effects via a different receptor-messenger system in the later. More specifically, a TGR5 agonist is a receptor ligand or compound that binds to TGR5 and increases the concentration of cyclic adenosine monophosphate (cAMP) by at least 20% in cells expressing the receptor." Conversely, a TGR5 antagonist would be a compound that antagonizes or blocks the activity of an agonist, thereby effecting a reduction in the concentration of cAMP The present invention relates to compounds having TGR5 receptor modulating activity and their use to treat and prevent metabolic diseases such as obesity and insulin sensitivity.

A compound of the invention is shown below.

| Compound No. | Structure |
|---|---|

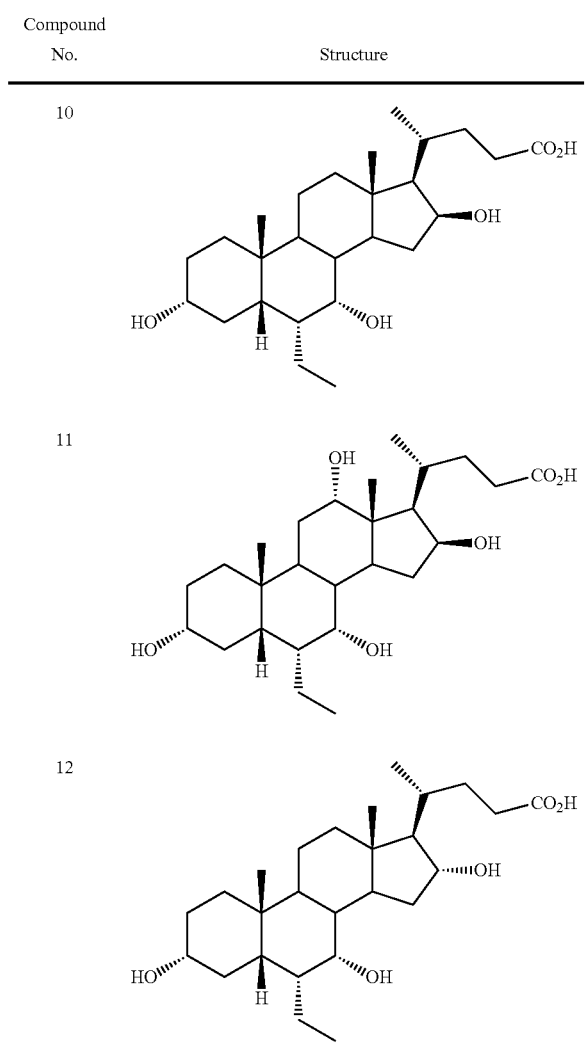

19

-continued

| Compound No. | Structure |
|---|---|
| 13 | 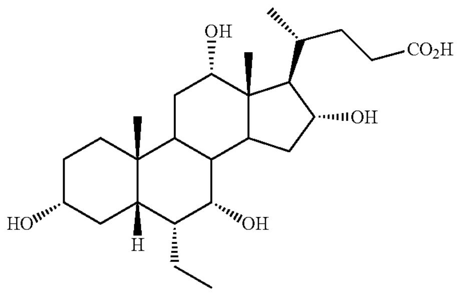 [SMILES: CC[C@H]1[C@@H](O)C2C3C[C@@H](O)[C@H]([C@H](C)CCC(=O)O)[C@@]3(C)[C@@H](O)CC2[C@@]2(C)CC[C@@H](O)C[C@@H]12] |
| 14 | 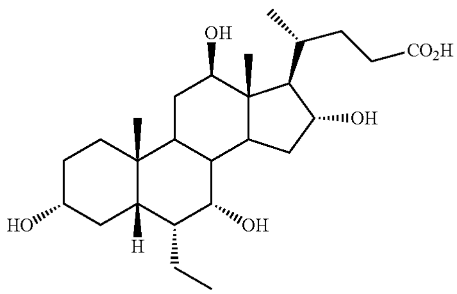 [SMILES: CC[C@H]1[C@@H](O)C2C3C[C@@H](O)[C@H]([C@H](C)CCC(=O)O)[C@@]3(C)[C@H](O)CC2[C@@]2(C)CC[C@@H](O)C[C@@H]12] |
| 15 | 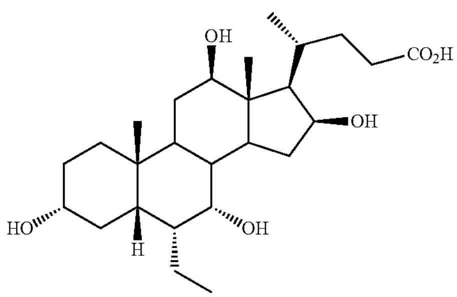 [SMILES: CC[C@H]1[C@@H](O)C2C3C[C@H](O)[C@H]([C@H](C)CCC(=O)O)[C@@]3(C)[C@H](O)CC2[C@@]2(C)CC[C@@H](O)C[C@@H]12] |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1

Synthesis of TGR5 Modulators

The compounds of the invention, and related derivatives, can be synthesized by methods known to one skilled in the art.

20

Synthesis of 3α,7α,16β-trihydroxy-6α-ethyl-5β-cholan-24-oic acid sodium salt (10)

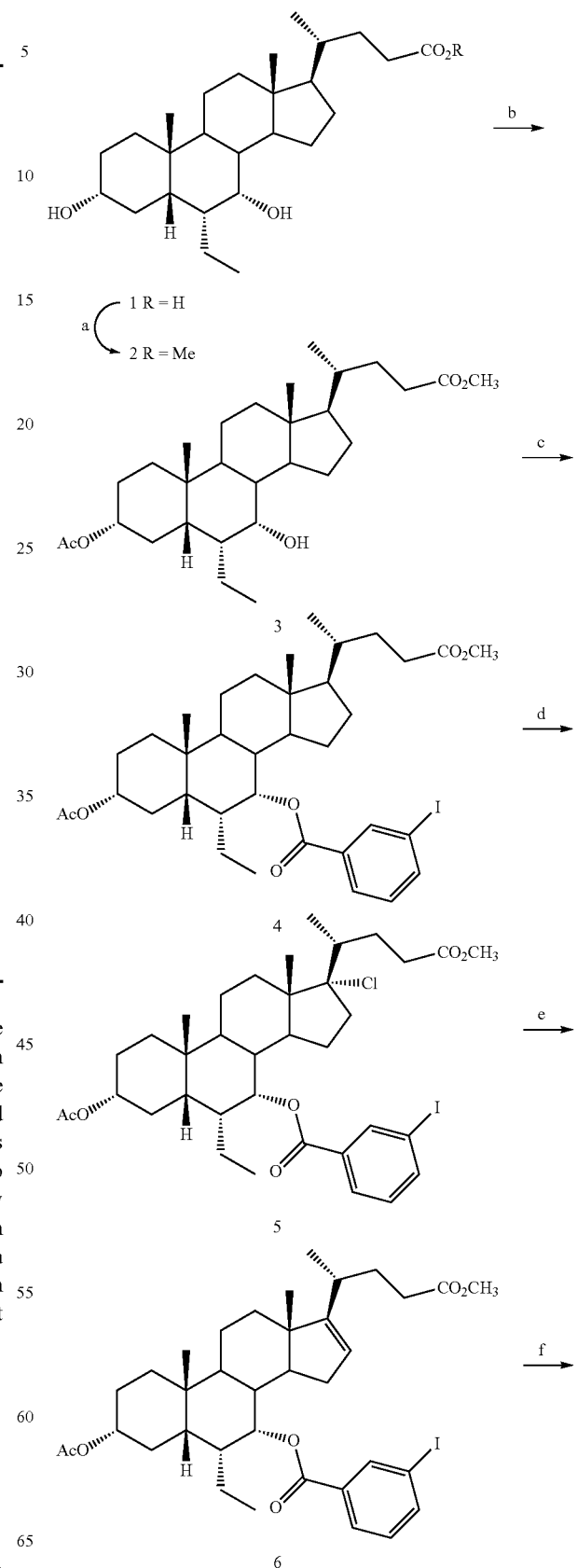

-continued

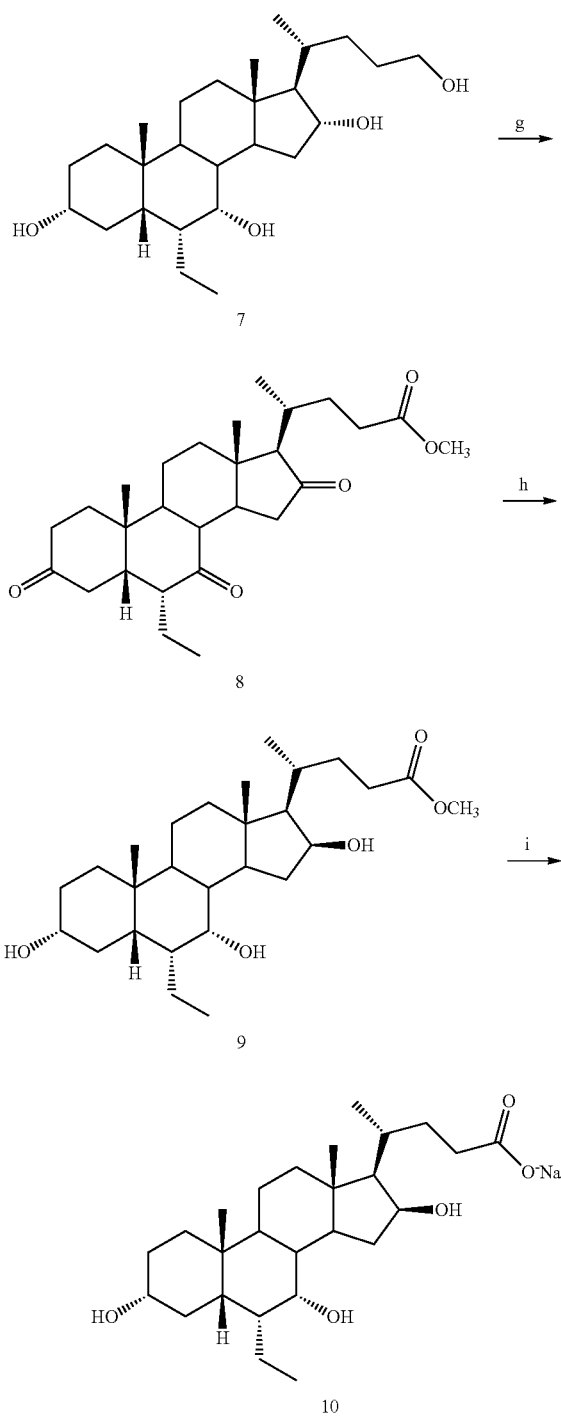

Reagent and conditions: a) MeOH, pTSA, ultrasound, 30° C., 2 h, 93%. b) Ac₂O, NaHCO₃, THF, reflux, 12 h, 99%. c) 1. 3-I-benzoic acid, (COCl)₂, CH₂Cl₂, rt, 1 h. 2. CaH₂, BnEt₃N⁺Cl⁻, toluene, reflux, 48 h, 80%. d) PhICl₂, ᵗBuOH, CH₂Cl₂, hv, 0° C., 1 h, 91%. e) Pyridine, reflux, 12 h, 64%. f) 1. BH₃THF, rt, 2 h. 2. H₂O₂, NaOH$_{acq}$, from 0° C. to rt, 3 h. 3. KOH, MeOH, toluene, reflux, 12 h. 47%. g) 1. Jones Reagent, acetone, from 0° C. to rt, 2 h. 2. pTSA, MeOH, ultrasound, 30° C., 2 h. 55%. h) ᵗBuNH₂BH₃, CH₂Cl₂, rt, 24 h, 40%. i) NaOH, MeOH, rt, 3 h, 82%. Overall Yield: 3.6%.

Methyl 3α, 7α-dihydroxy-6α-ethyl-5β-cholan-24-oate (2)

To a solution of 1 (4.1 g, 9.76 mmol) in methanol (120 ml) pTSA (0.41 g, 2.15 mmol) was added and the mixture was sonicated at 30° C. for 2 h. The solvent was evaporated under reduce pressure, the residue was dissolved in CHCl₃ (150 ml), washed with a saturated aqueous solution of sodium bicarbonate (2×100 ml), water (100 ml) and brine (100 ml). The organic layer was dried on anhydrous sodium sulfate and evaporated to dryness to afford the methyl ester 2 (3.95 g, 9.1 mmol, 93% l) as white solid that was used for the following step without further purification.

Methyl 3a-acetoxy-7a-hydroxy-6a-ethyl-5β-cholan-24-oate (3)

To a solution of 2 (3.9 g, 8.98 mmol) in freshly distillate THF (100 ml) acetic anhydride (15.29 ml, 161.75 mmol) and NaHCO₃ (15.09 g, 179.72 mmol) were added and the resulting mixture was refluxed overnight. The mixture was cooled to room temperature, diluted with water (120 ml) and extracted with EtOAc (3×80 ml). The combined organic layers were washed with water (2×100 ml), brine (100 ml), dried over anhydrous sodium sulfate and evaporated to dryness under reduced pressure to get the desired acetylated compound 3 (4.25 g, 8.92 mmol, 99%) as white solid that was used for the next step without further purification.

¹H-NMR (CDCl₃) δ: 0.65 (3H, s, 18-CH₃), 0.84-0.93 (9H, m, 19-CH₃+21-CH₃-21, 26-CH₃), 1.11-1.91 (26H, m), 2.00 (3H, s, 3-CHOC(O)CH₃), 2.28-2.36 (2H, m), 3.65 (3H, s, COOCH₃), 3.70 (1H, bs, 7-CH), 4.48-4.59 (1H, m, 3-CH).

Methyl 3α-acetoxy-6α-ethyl-7α-(3'-iodobenzoyl)oxy-5β-cholan-24-oate (4)

3-Iodobenzoic acid (3.93 g, 15. mmol) was suspended in CH₂Cl₂ (30 ml) and treated with oxalyl chloride (3.21 ml, 36.1 mmol) in the presence of 2 drops of DMF at room temperature until the mixture become dissolved (about 1 h). Volatiles were removed under reduced pressure and the acylc chloride thus obtained was dissolved in 150 ml of toluene and was added to a stirred solution of 3 (4.2 g, 8.82 mmol) in toluene (150 ml). To the above solution, CaH₂ (2.66 g, 63.5 mmol) and BnEt₃N+Cl— (0.5 g, 2.2 mmol) were added, and the mixture was refluxed for 48 h. The reaction mixture was then cooled to room temperature, the solvent was evaporated under reduced pressure, the residue was suspended in CHCl₃ (200 ml) and filtered. The organic filtrate was washed with a saturated solution of sodium bicarbonate (2×100 ml), water (100 ml), brine (100 ml), dried over anhydrous sodium sulphate and evaporated to dryness. The residue was purified by flash chromatography using from 5 to 10% of EtOAc in petroleum ether to yield 3.54 g (5.01 mmol, 57%) of 4 and 1.23 g (2.58 mmol) of unreacted started material (conversion yield 80%).

¹H-NMR (CDCl₃) δ: 0.67 (3H, s, 18-CH₃), 0.88-0.92 (6H, m, 21-CH₃, 26-CH₃), 1.13-1.32 (15H, m), 1.7-1.74 (5H, m), 1.89-1.91 (5H, m), 2.05 (3H, s, 3-CHOC(O)CH₃), 2.18-2.30 (2H, m), 3.63 (3H, s, COOCH₃), 4.60-4.62 (1H, m, 3-CH), 5.41 (1H, bs, 7-CH), 7.23 (1H, dd, J1=6.5 Hz, J2=6.7 Hz, 5'-H), 7.94 (1H, d, J=6.7 Hz, 4'-H), 8.04 (1H, d, J=6.5 Hz, 6'-H); 8.37 (1H, s, 2'-H).

¹³C-NMR (CDCl₃) δ: 11.6, 11.7, 18.2, 20.7, 21.7, 22.2, 23.1, 23.9, 26.8, 27.9, 29.6, 30.8 (x2), 34.4, 35.1 (2x), 35.5, 39.2, 39.3, 41.3, 42.9, 44.6, 50.6, 51.4, 55.3, 74.2, 74.5, 93.9, 128.9, 130.1, 132.4, 138.6, 141.6, 164.5, 170.3, 174.6.

Methyl 3α-acetoxy-6α-ethyl-7α-(3'-iodobenzoyl)oxy-17a-chloro-5β-cholan-24-oate (5)

To a solution of 4 (3.5 g, 4.95 mmol) in $CH_2Cl_2$ (280 ml) containing 0.3 M $^tBuOH$ (8.2 ml), dichloroiodobenzene (3.38 g, 12.4 mmol) was added. The mixture was deoxygenated for 3 min by bubbling dry $N_2$. Then the mixture was photolyzed at 0° C. using a tungsten lamps (200 W) for 1 h. The solvent was then evaporated under reduced pressure and the residue was quickly purified by flash chromatography eluting with petroleum ether/EtOAc (8:2, v/v) to yield 3.35 g (4.52 mmol, 92%) of the 17-chloro derivative 5 as white solid.

$^1$H-NMR ($CDCl_3$) δ: 0.81 (3H, s, 18-$CH_3$), 0.91 (3H, d, J=7.3 Hz, 21-$CH_3$), 1.0 (6H, m, 19-$CH_3$+26-$CH_3$), 1.12-1.93 (24H, m), 2.03 (3H, s, 3-CHOC(O)$CH_3$), 2.18-2.25 (2H, m), 3.65 (3H, s, COO$CH_3$), 4.57-4.62 (1H, m, 3-CH), 5.40 (1H, bs, 7-CH), 7.22 (1H, t, J=7.79 Hz, 5'-H), 7.91 (1H, d, J=7.76 Hz, 4'-H), 8.02 (1H, d, J=7.7 Hz, 6'-H), 8.38 (1H, s, 2'-H).

$^{13}$C-NMR ($CDCl_3$) δ: 11.6, 14.4, 14.5, 20.7, 21.6, 22.2, 23.1 (x2), 26.7, 28.6, 29.4, 31.7, 34.2 (x2), 35.1, 35.4, 39.6, 40.4, 41.1, 41.3, 44.6, 45.2, 49.9, 51.5, 74.1, 74.4, 92.9, 93.9, 128.8, 130.1, 132.3, 138.6, 141.7, 164.9, 170.7, 174.1.

Methyl $\Delta^{16}$ 3α-acetoxy-6α-ethyl-7α-(3'-iodobenzoyl)oxy-5β-cholan-24-oate (6)

The 17-chloro derivative 5 (3.3 g, 4.46 mmol) was dissolved in dry pyridine (130 ml) and refluxed overnight. The solvent was then evaporated under reduced pressure and the residue was purified by flash chromatography eluting with petroleum ether/EtOAc 8:2 to yield 2.24 g (3.18 mmol, 72%) of the desired olefin as white solid.

$^1$H-NMR ($CDCl_3$) δ: 0.75 (3H, s, 18-$CH_3$), 0.89 (3H, t, J=7.4 Hz, 21-$CH_3$), 0.98 (3H, t, J=6.5 Hz, 26-$CH_3$), 1.03 (H, s, 19-$CH_3$), 1.11-2.02 (22H, m), 2.05 (3H, s, 3-CHOC(O)$CH_3$), 2.22-2.30 (2H, m), 3.65 (3H, s, COO$CH_3$), 4.58-4.62 (1H, m, 3-CH), 5.20 (1H, bs, 7-CH), 5.51 (1H, s, 16-CH), 7.21 (1H, t, J=7.9 Hz, 5'-H), 7.90 (1H, dt, J1=7.9 Hz, J2=1.1 Hz, 4'-H), 8.02 (1H, dt, J1=7.9 Hz, J2=1.1 Hz, 6'-H), 8.37 (1H, t, J=1.3 Hz, 2'-H).

$^{13}$C-NMR ($CDCl_3$) δ: 11.6, 15.9, 20.6, 21.7, 21.8, 22.1, 23.1, 26.7, 29.6, 30.9, 31.1, 31.7, 32.2, 34.5, 34.9, 35.0, 35.7, 37.9, 41.3, 44.8, 47.5, 51.4, 51.7, 74.1, 74.7, 93.9, 121.4, 128.9, 130.1, 132.3, 138.6, 141.7, 158.5, 164.6, 170.7, 174.4.

3α,7α,16α,24-tetrahydroxy-6α-ethyl-5β-cholane (7)

The olefin 6 (0.3 g, 0.42 mmol) was dissolved in $BH_3$-THF (10.6 ml 1M in THF) at 0° C. and then stirred at room temperature for 2 h. After this time the reaction was cooled at 0° C. and a mixture of 4M aqueous NaOH (20 ml) and $H_2O_2$ (20 ml) was added dropwise and the resulting mixture was stirred at this temperature for 3 h. The reaction was acidified with 1N HCl and extracted with $CH_2Cl_2$ (3×60 ml). The combined organic layers were dried over anhydrous sodium sulphate and evaporated to dryness under reduced pressure. The oily residue was dissolved in toluene (52 ml), 5% KOH in MeOH (7 ml) was added and the resulting mixture was refluxed overnight. The solvent was removed under reduce pressure, the residue was dissolved in water (25 ml) and extracted with EtOAc (3×30 ml). The combined organic layers were dried over anhydrous sodium sulphate and evaporated to dryness under reduced pressure. The residue was purified by flash chromatography eluting with EtOAc/EtOH (95:5, v/v) to yield 0.085 g (0.2 mmol, 47%) of the desired tetrol as white solid.

$^1$H-NMR ($CDCl_3$) δ: 0.64 (3H, s, 18-$CH_3$), 0.85-0.91 (6H, m, 19-$CH_3$+26-$CH_3$), 0.92 (3H, d, J=6.4 Hz, 21-$CH_3$), 1.21-1.91 (21H, m), 3.33-3.35 (1H, m, 3-CH), 3.54-3.61 (3H, m, 7-CH+24-$CH_2$), 3.94 (1H, bs, 16-CH).

$^{13}$C-NMR ($CDCl_3$) δ: 11.7, 13.1, 14.1, 18.8, 20.4, 21.9, 22.4, 23.1, 28.7, 30.4, 31.8, 33.1, 33.5, 34.0, 35.4 (x2), 35.5, 35.8, 39.5, 39.9, 41.3, 43.9, 45.3, 47.4, 62.6, 66.1, 70.6, 72.0.

Methyl 3,7,16-trioxo-6α-ethyl-5β-cholan-24-oate (8)

Jones reagent (2 ml) was added dropwise to a stirred solution of the tetrol 7 (0.19 g, 0.45 mmol) in acetone (25 ml) at 0° C. and the mixture was stirred at room temperature for 1 h. Methanol (8 ml) was then added and the oxidized product was extracted with EtOAc (2×50 ml). The combined organic layers were dried over anhydrous sodium sulphate and evaporated to dryness under reduced pressure. The residue was dissolved in MeOH (80 ml), pTSA was added and the mixture was stirred at room temperature for 2 h. The solvent was evaporated under reduce pressure, the residue was dissolved in $CHCl_3$ (50 ml), washed with a saturated aqueous solution of sodium bicarbonate (2×50 ml), water (50 ml) and brine (50 ml). The organic layer was dried over anhydrous sodium sulfate and evaporated to dryness. The residue was purified by flash chromatography using from 20 to 30% EtOAc in petroleum ether to afford the methyl ester 8 (0.115 g, 0.26 mmo, 58%1) as whitish solid.

$^1$H-NMR ($CDCl_3$) δ: 0.82 (3H, s, 18-$CH_3$); 0.85 (3H, m, 26-$CH_3$); 1.0 (3H, d, J=6.5 Hz, 21-$CH_3$); 1.37 (3H, s, 19-$CH_3$); 1.55-2.35 (23H, m); 2.63-2.87 (2H, m).

Methyl 3α,7α,16β-trihydroxy-6α-ethyl-5β-cholan-24-oate (9)

To a solution of the triketo ester 8 (0.1 g, 0.22 mmol) in $CH_2Cl_2$ (8 ml) tert-butylamine-borane complex (0.1 g, 1.12 mmol) was added and the reaction was refluxed overnight. The reaction was cooled to room temperature 3N HCl was added and the resulting mixture was stirred for 30 min. The organic layer was separated, washed with a saturated aqueous solution of sodium bicarbonate (10 ml), water (10 ml), was dried over anhydrous sodium sulfate and evaporated to dryness. The residue, in which the 7-ketone was not reduced, was dissolved in a mixture 1:4 v/v of $H_2O$/THF (5 ml) and $NaBH_4$ was added at 0° C. The mixture was stirred at room temperature for 30 min, then water (5 ml) and 3N HCl (5 ml) were added. The mixture was extracted with EtOAc (4×30 ml), the combined organic layers were dried over anhydrous sodium sulphate and evaporated to dryness under reduced pressure. The residue, which consist of at least 2 components, was purified by flash chromatography, using from 1 to 4% MeOH in $CHCl_3$ to yield 0.036 g (0.08 mmol, 36%) of the desired compound 9.

$^1$H-NMR (Aceton-d6) δ: 0.87-0.90 (6H, m, 18-$CH_3$+26-$CH_3$), 0.92 (3H, s, 19-$CH_3$), 0.98 (3H, d, J=6.4 Hz, 21-$CH_3$), 1.19-1.58 (10H, m), 1.75-2.05 (7H, m), 2.34-2.41 (2H, m) 3.28-3.30 (1H, m, 3-CH), 3.62 (3H, s, COO$CH_3$), 3.64 (1H, bs, 7-CH), 4.37 (1H, bs, 16-CH).

$^{13}$C-NMR (Aceton-d6) δ: 11.1, 12.5, 17.4, 20.4, 22.3, 22.8, 30.1, 30.4, 30.5, 30.6, 33.1, 33.7, 35.4, 35.6 (x2), 39.7, 40.0, 41.6, 42.2, 45.7, 48.3, 50.8, 61.7, 69.5, 71.3, 71.4, 174.8.

3α,7α,16β-trihydroxy-6α-ethyl-5β-cholan-24-oic acid sodium salt (10)

The ester 9 (35 mg, 0.08 mmol) was dissolved in 8 ml of 5% NaOH in MeOH and the resulting mixture was stirred at room temperature over night. The solvent was evaporated under reduced pressure, the resulting solid was in a mixture of $H_2O/CH_3OH$ (1:1) and purified by reverse phase chromatography (column RP-18 lobar A) using a mixture of $CH_3OH/H_2O$ (from 5:5 to 7:3) as mobile phase, to afford the desired sodium salt 10 (15 mg, 0.03 mmol, 43%).

$^1$H-NMR (CD$_3$OD) δ: 0.86 (3H, s, 18-CH$_3$), 0.88-0.93 (6H, m, 19-CH$_3$+26-CH$_3$), 0.99 (3H, d, J=6.4 Hz, 21-CH$_3$), 1.06-1.41 (9H, m), 1.46-1.9 (11H, m), 1.97-2.04 (2H, m), 2.23-2.25 (2H, m), 2.30-2.35 (1H, m), 3.28-3.35 (1H, m, 3-CH), 3.67 (1H, bs, 7-CH), 4.49-4.52 (1H, m, 16-CH).

$^{13}$C-NMR (CD$_3$OD) δ: 12.0, 13.3, 18.7, 21.6, 23.5, 23.7, 29.5, 31.2, 31.3, 33.4, 34.4, 34.5, 35.3, 35.5, 36.6, 36.7, 41.2, 43.1, 43.4, 46.7, 63.8, 71.1, 73.2, 73.4.

Example 2

In Vitro TGR5 and FXR Activity

Example 2A

TGR5 and FXR Receptor Binding

The potency and efficacy of compounds of the invention on TGR5 receptor is evaluated using in vitro assays. Table 1 summarizes the potency and efficacy of a compound of the invention on FXR and TGR5 Receptors

TABLE 1

| | Alphascreen Assay | FRET (cAMP) NCI-H716 | Transactivation Assay | FRET-cAMP on TGR5 overexpressing Hek293 cells |
|---|---|---|---|---|
| Compound (Reference Standard) | hFXR (CDCA = 10-20 µM) EC$_{50}$ (µM) | hTGR5 (LCA = 4-8 µM) EC$_{50}$ (µM) | hTGR5 (LCA = 1-6 µM) EC$_{50}$ (µM) | hTGR5 (LCA = 0.3-5 µM) EC$_{50}$ (µM) |
| Compound 10 | 12 | 0.65 | 0.04 | 0.2 |

FRET Assay (Detection of Intracellular cAMP Levels).

The receptor binding assay was performed by measuring the level of cyclic AMP (cAMP) using FRET assay. Human intestinal cell lines (NCI-H716) were plated in 96-well plates coated with 0.75 mg/ml Matrigel (BD Biosciences) according to manufacturer's instructions just prior to use, at a density of 12×10$^3$ cells/well in DMEM supplemented with 10% (v/v) FBS, 100 units/ml penicillin and 100 µg/ml streptomycin sulfate, and cultured for 24 h, which allowed cell adhesion to the bottom of the plate. The cells were washed twice with PBS and medium was exchanged for cAMP assay medium [OPTIMEM containing 0.1% (w/v) BSA and 1 mM 3-isobutyl-1-methylxanthine (IBMX)]. After incubation for 60 minutes at 37° C., the cells were treated with increasing concentrations of compound 10 in stimulation buffer (5 mM HEPES, 0.1% BSA in HBSS pH 7.4) containing the europium chelate—Streptavidin and the ALEXA Fluor 647-conjugated antibody anti-cAMP (PerkinElmer) for 1 hour at room temperature. The level of intracellular cAMP was determined with Lance kit (PerkinElmer). Litocholic acid was used as control ligand. Z' factor was used to validate assays. Non linear regression curves, without constraints, were performed by using four parameter equation and GraphPad Prism Software (GraphPad Inc.), to obtain the EC50 values.

Alphascreen Assay

Activity on FXR was assayed by using Alphascreen technology in a coactivator recruitment assay. AlphaScreen is a bead-based chemistry assay used to study biomolecular interactions. Binding of molecules captured on the beads leads to an energy transfer from one bead to the other, ultimately producing a luminescent signal. When the partners interact, chemical energy is transferred from Donor to Acceptor beads and a signal is produced. Upon bile acids stimulation the GST-FXR-LBD interacts with the Src-1 peptide. Anti-GST-coated Acceptor beads were used to capture the GST-fusion FXR-LBD whereas the biotinylated-SRC-1 peptide was captured by the streptavidin Donor beads. Upon illumination at 680 nm chemical energy is transferred from Donor to Acceptor beads across the complex streptavidin-Donor/Src-1-Biotin/GSTFXR-LBD/Anti-GST-Acceptor and a signal is produced. The assay was performed in white, low-volume, 384-well Optiplates (PerkinElmer) using a final volume of 25 µl containing final concentrations of 10 nM of purified GST-tagged FXR-LBD protein, 30 nM biotinylated Src-1 peptide, 20 µg/ml anti-GST acceptor beads acceptor beads and 10 µg/ml of streptavidin donor bead (PerkinElmer). The assay buffer contained 50 mM Tris (pH 7.4), 50 mM KCl, 0.1% BSA, and 1 mM DTT. The stimulation times with 1 µl of ligands (solubilized in 100% DMSO) were fixed to 30' a room temperature. The concentration of DMSO in each well was maintained at a final concentration of 4%. After the addition of the detection mix (acceptor and donor beads), the plates were incubated in the dark for 4 h at room temperature and then were read with an Envision microplate analyzer (PerkinElmer). Dose response curves were performed in triplicate and Z' factor was used to validate the assays. Non linear regression curves, without constraints, were performed by using four parameter equation and GraphPad Prism Software (GraphPad Inc.), to obtain the EC50 values.

Cell Culture, Transfection and Luciferase Assay

HEPG2 and HEK293T cells were cultured in E-MEM and DMEM respectively, either supplemented with 1% penicillin/streptomycin, 1% L-glutamine and 10% fetal bovine serum. (high glucose) (Invitrogen, Carlsbad, Calif.). Cells were grown at 37° C. in 5% CO$_2$. All the transfections were made using 5:2 Fugene HD Trasfection reagent (µl) to DNA (µg) respectively (Roche). Twenty-four hours before transfection HEK293T or HepG2 cells were seeded onto a 96-well plate at a density of 10.000 or 15.000 cells/well, respectively. Transient transfections were performed using 100 ng of reporter vector pGL4.29[luc2P/CRE/Hygro] (Promega), 40 ng of pGL4.74 (Renilla), as internal control for transfection efficiency, and 10 ng of expression plasmid pCMV-SPORT6-hTGR5 The NIH Mammalian Gene Collection clone MGC: 40597 (Invitrogen). The pGEM vector was added to normalize the amounts of DNA transfected in each assay (2 µg). Twenty-four hours post-transfection the cells were stimulated with increasing concentrations of compound 10 for 18 h. Control cultures received vehicle (0.1% DMSO) alone. The cells were then lysed by adding 75 µl of Dual-Glo Luciferase Reagent (Promega) to 75 µl of medium containing cells/well. Renilla luciferase activity was measured by adding volume:volume of Dual-Glo Stop & Glo reagent and original culture medium. Luciferase activities were expressed as ratio between luciferase unit and renilla luciferase unit. Each data point is the average of triplicate assays. Each experiment was repeated at least three times.

50% Effective Concentrations (EC50) and Efficacy Determination

Efficacy was determined by calculating percentages of 10 µM LCA value for TGR5 agonist study and 10 µM CDCA value for FXR agonist study, respectively. After subtracting the average value of the basal (vehicle-treated) condition, values were applied to EC$_{50}$ and/or efficacy determinations.

Calculation of average $EC_{50}$ and comparison of the $EC_{50}$ between different compounds were done after transformation to logarithms.

Example 2B

TGR5 Target Gene Expression Assay of Compound 10

Figure 3:
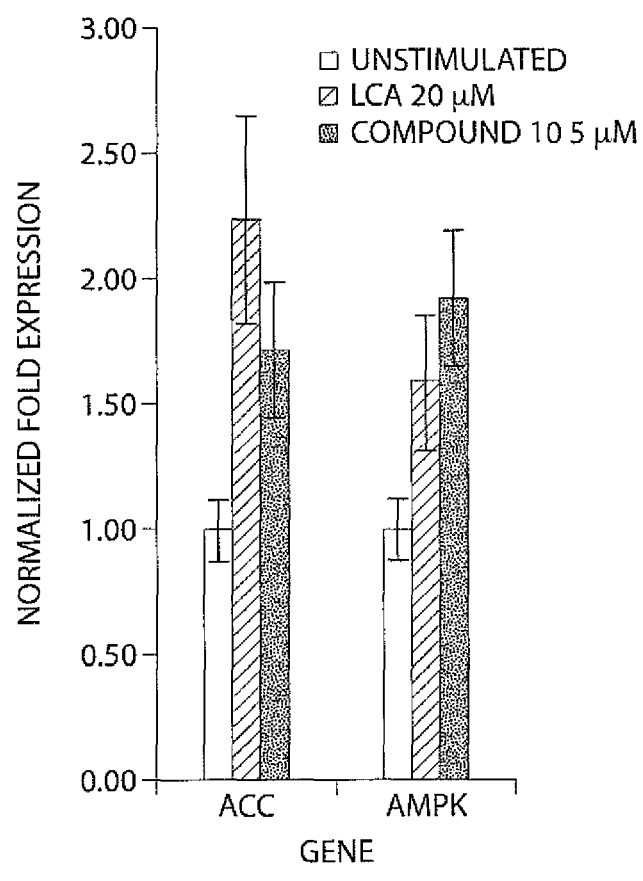
FIG. 3 is a bar graph that shows the results of TGR5 target gene expression assay for compound 10 using intestinal NCI-H716 cells and LCA as a positive control.

The level of ACC and AMPK gene expression in intestinal NCI-H716 cells was measured using compound 10 and LCA as positive control. The mRNA expression level of TGR-5 target genes was measured by Real-Time Polymerase Chain Reaction (Q-RTPCR). Total RNA was isolated (Aurum Total RNA Mini Kit BioRad) from NCI-H716 stimulated with 5 µM compound 10 for 18 hours. The RNA was randomly reverse-transcribed with ISCRIPT cDNA SYNTHESIS KIT (BioRad) in 20 µl reaction volume. Ten ng template was used in 20 µl final volume reaction of Real-Time PCR containing 0.3 µM of each primer and 10 µl of 2×SYBR Green PCR Master MIX (Bio-Rad). All reactions were performed in triplicate and the thermal cycling conditions were: 3 minutes at 95° C., followed by 45 cycles of 95° C. for 10 seconds, and 60° C. for 30 seconds in iCycler iQ5 instrument (Biorad, Hercules, Calif.). The mean value of the replicates for each sample was calculated and expressed as cycle threshold (CT: cycle number at which each PCR reaction reaches a predetermined fluorescence threshold, set within the linear range of all reactions). The amount of gene expression was then calculated as the difference (ΔCT) between the CT value of the sample for the target gene and the mean CT value of that sample for the endogenous control β2-Microglobulin. Relative expression was calculated as the difference (ΔΔCT) between the ΔCT values of the test sample and of the control sample (WT) for each target gene. The relative quantitation value was expressed and shown as 2-ΔΔCT. All PCR primers were intron spanning designed using the software Beacon Designer on published sequence data from the NCBI database. The results are shown in FIG. 3.

Example 2C

Figure 4A:
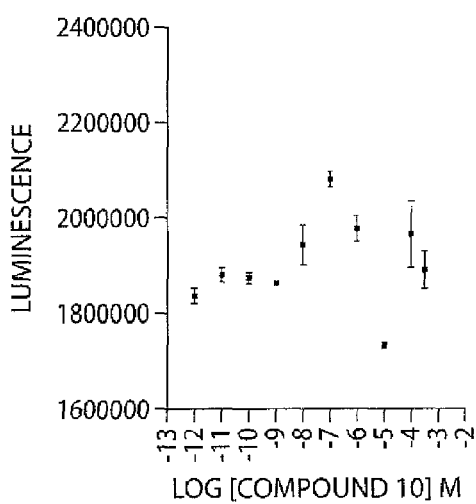
FIG. 4 is a series of 3 graphs (A-C) that show the results for compound 10 of in vitro cytotoxicity testing measuring ATP-release after 4 hours of stimulation using human intestinal (NCI-H716). LCA is a positive control.
Figure 4B:
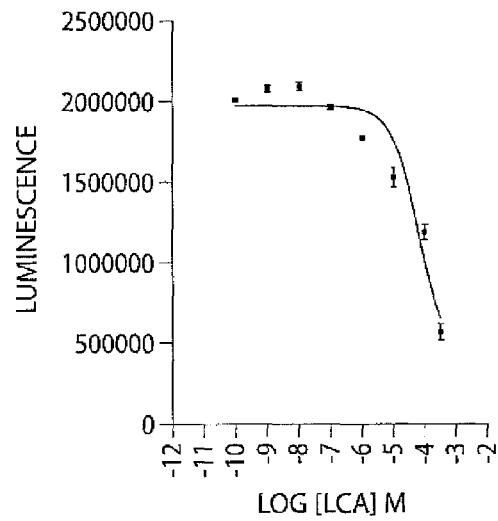
Figure 4C:
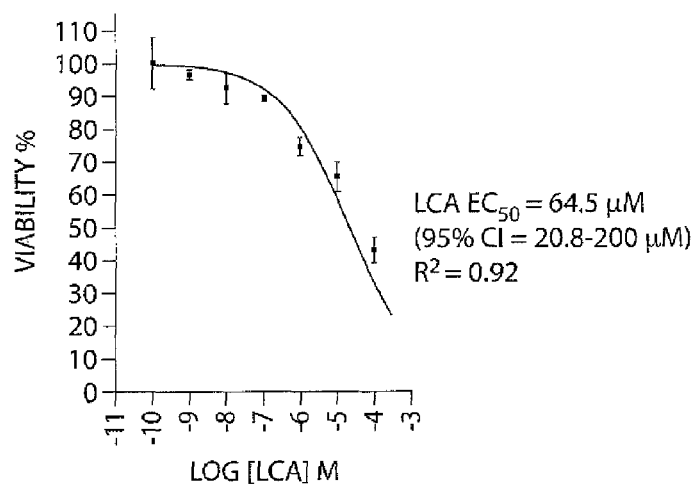

In Vitro Cytotoxicity of Compound 10 in Human Intestinal and Hepatic Cell Lines Cell viability was measured using Perkinelmer ATP-Lite 1 STEP. ATP is a marker for cell viability because it is present in all metabolically active cells and the concentration declines very rapidly when the cells undergo necrosis or apoptosis. Human NCI-H716 or HepG2 cells ($1 \times 10^4$) were seeded in 96 wells plate and stimulated with 10-fold dilutions from 1 nM to 300 µM of the compound 10 for 4 h at 37° C. The plates were equilibrated at RT for 10 minutes and 100 µl of ATP-Lite 1 STEP Reagent was added to 100 µl of culture medium containing cells. Luminescence was read with Victor Light (PerkinElmer). The experimental signal was subtracted from background. Tamoxifen was used as a positive control of cellular cytotoxicity, while untreated cells served as negative control. The results are shown in FIGS. 4 and 5.

Example 3

Metabolic Activities of Compounds of the Invention in a Diet-Induced Obesity Mouse Model The goal of the study is to define whether TGR5 agonists (oleanolic acid (OA) or compound of the invention (for example, a "test compound")) correct the development of obesity and associated insulin-resistance in vivo. To test this possibility, OA/test compound are administered via food administration for 16 weeks to male C57BL6J mice that were previously subjected for 10 weeks to a high fat diet.

II—Protocol

In a previous study, OA was observed as a selective TGR5 agonist that did not cause food aversion. Animals treated with a dose of 100 mg/kg/day of OA showed, however, some signs of toxicity, whereas a lower dose was well tolerated. Therefore, OA is administered at the dose of 50 mg/kg/d in this study.

In vitro studies have identified compounds of the invention as potent and selective TGR5 ligands. No problems with toxicity are expected with compounds of the invention, which are administered at ~50-fold lower concentration.

For this study, 48 male C57BL6J mice (5 weeks of age) are divided in two groups: one group of 24 (group 1, 2&3) animals receives chow diet whereas the other group of 24 receives a high fat diet for a period of 10 weeks (group 4,5&6). The animals are then analyzed during a period of 16 weeks. Five groups of 10 animals are assigned as follows:
1: chow diet
2: chow diet+OA 50 mg/kg/day
3: chow diet+test compound e.g., 30 mg/kg/day
4: high fat diet
5: high fat diet+OA 50 mg/kg/day
6: high fat diet+test compound e.g., 30 mg/kg/day
During the entire study, body weight and food intake are monitored twice weekly.

Week-2: Body composition is analyzed, for all groups, by dual energy X-ray absorptiometry (dexascan).

Week-1: Serum levels of transaminases, glucose, triglycerides, cholesterol, HDL-C, LDL-C and insulin are measured in all groups after a fasting period of 12 h and mice are then placed on the diets as indicated (Day 0).

Week 2: Serum levels of transaminases, glucose, triglycerides, cholesterol, HDL-C, LDL-C and insulin are measured in all groups after a fasting period of 12 h (Day 14).

Week 4: Glucose tolerance is determined by subjecting all the animals to an intraperitoneal glucose tolerance test (IP-GTT). Animals are fasted for 12 h prior to this test. Nocturnal energy expenditure of groups 1, 4, 5 and 6 (chow diet, high fat diet and high fat diet OA/test compound are measured by indirect calorimetry.

Week 8: Body weight composition is again analyzed by dexascan for all groups. Serum levels of transaminases, glucose, triglycerides, cholesterol, HDL-C, LDL-C and insulin are measured in all groups after a fasting period of 12 h (Day 56).

Week 9: Circadian activity of groups 4, 5 and 6 (high fat diet fed mice) is studied during a period of 30 h.

Week 10: Measurement of blood pressure and heart rate is performed on groups 4, 5 and 6.

Week 11: Rectal temperature of all animals is measured at room temperature at 10:00 am.

Circadian activity measurement is performed on groups 1, 2, 3 and 4.

Week 12: Glucose tolerance is analyzed by performing an intraperitoneal glucose tolerance test (IPGTT) on groups 4, 5 and 6. During the IPGTT, blood is also collected to analyze insulin levels. Animals are fasted 12 h prior to these tests. Feces are collected in all groups over a 24 h time period and fecal lipids content is measured.

Week 16: Cold test is performed on all animals by measuring body temperature of animals exposed to 4° C.

Three days later, animals are sacrificed. At sacrifice, blood is collected and analyzed for: plasma lipids (TC, TG, HDL-C, FFAs); liver functions (ALAT, ASAT, alkaline Pase, γ-GT); glucose and insulin; lipoprotein profiles of selected groups of plasma (size-exclusion chomatography).

Liver, small intestine, adipose tissues (WAT and BAT), pancreas, heart and muscle are collected, weighed and kept for further analyses including: standard histology (HE staining, succinate dehydrogenase staining, oil-red-0 staining and cell morphology); tissue lipid content; electron microscopy on BAT and muscle to analyze mitochondria; RNA isolation for expression studies of selected genes involved in metabolism and energy homeostasis by quantitative RT-PCR; Protein extraction for the study of post-translationnal modifications such as acetylation of proteins of interest (e.g. PGC-1α).

III—Detailed Procedures

A—Animal Procedure and Diets

Animals Housing and Handling

Mice are group housed (5 animals/cage) in specific pathogen-free conditions with a 12 h:12 h (on at 7:00) light-dark cycle, in a temperature (20-22° C.) and humidity controlled vivarium, according to the European Community specifications. Animals are allowed free access to water and food.

Drinking Water

Chemical composition of the tap water is regularly analyzed to verify the absence of potential toxic substances at the Institut d'Hydrologie, ULP, Strasbourg. Drinking water is treated with HCl and $HClO_4$ to maintain pH between 5 and 5.5 and chlorin concentration between 5 and 6 ppm.

Diet

The standard rodent chow diet is obtained from UAR and the high fat diet is obtained from Research Diet. Mice are fed, either with chow diet (16% protein, 3% fat, 5% fiber, 5% ash) or with high fat diet (20% protein, 20% carbohydrate, 60% fat). Oleanolic acid and test compound were mixed with either powdered chow diet or either powdered high fat diet in the following proportions: 0.5 g of OA/kg of food for the 50 mg/kg/day treatment and 0.08 g of test compound/kg of food for the 10 mg/kg/day treatment. Pellets are then reconstituted. Control groups receive food pellets without test compound or OA. Due to the consistency of the high fat diet, no water is added in the mix with OA. In the case of the chow diet, which is harder to reconstitute, a minimal amount of water is added to the powder to reconstitute pellets, which are then air-dried. New batches of food are prepared weekly.

Blood Collection

Blood is collected either from the retro-orbital sinus under anesthesia or from the tail vein.

Anesthesia

For the dexa scanning experiment, animals are anesthesized with a mixture of ketamine (200 mg/kg)/Xylasine (10 mg/kg) administered by intra-peritoneal injection. For the venipuncture, animals are anesthesized by inhalation of an isoflurane-$O_2$ mixture.

B—Biochemistry

The tests are performed with an Olympus AU-400 automated laboratory work station using commercial reagents (Olympus).

Analysis of Lipids and Lipoproteins

Serum triglycerides, total and HDL cholesterol are determined by enzymatic assays. Serum HDL cholesterol content are determined after precipitation of apo B-containing lipoproteins with phosphotungstic acid/Mg (e.g., Roche Diagnostics, Mannheim, Germany). Free fatty acids level are determined with a kit from Wako (e.g., Neuss, Germany) as specified by the provider.

Metabolic and Endocrine Exploration

Blood glucose concentration is measured by a Precision Q.I.D analyzer (e.g., Medisense system), using Medisense Precis electrodes (e.g., Abbot Laboratories, Medisense products, Bedford, USA). This method is validated, by comparing Precision Q.I.D analyzer values with classical glucose measurements. The Precision Q.I.D method was chosen since it requires a minimal amount of blood and can hence be employed for multiple measurements such as during an IPGTT. Plasma insulin (e.g., Mercodia, Uppsala, Sweden) is determined by ELISA according to the manufacturer's specifications.

C-Metabolic Testing

Lipoprotein Profiles

Lipoprotein profiles are obtained by fast protein liquid chromatography, allowing separation of the three major lipoprotein classes VLDL, LDL, and HDL.

Intraperitoneal Glucose Tolerance Test (IPGTT)—Oral Glucose Tolerance Test

IPGTT is performed in mice which are fasted overnight (12 h). Mice are either injected intraperitoneally (IPGTT) with a solution of 20% glucose in sterile saline (0.9% NaCl) at a dose of 2 g glucose/kg body weight. Blood is collected from the tail vein, for glucose and insulin monitoring, prior and 15, 30, 45, 75, 90, 120, 150, 180 min after administration of the glucose solution. The incremental area of the glucose curve is calculated as a measure of insulin sensitivity, whereas the corresponding insulin levels indicate insulin secretory reserves.

Energy Expenditure

Energy expenditure is evaluated through indirect calorimetry by measuring oxygen consumption with the Oxymax apparatus (e.g., Columbus Instruments, Columbus, Ohio) during 12 h. This system consists of an open circuit with air coming in and out of plastic cages (one mouse per cage). Animals are allowed free access to food and water. A very precise $CO_2$ and $O_2$ sensor measures the difference in $O_2$ and $CO_2$ concentrations in both air volumes, which gives the amount of oxygen consumed in a period of time given that the air flow of air coming in the cage is constant. The data coming out of the apparatus is processed in a connected computer, analyzed, and shown in an exportable Excel file. The values are expressed as $ml \cdot kg^{-1} \cdot h^{-1}$, which is commonly known as the $VO_2$.

Determination of Body Fat Content by Dexa Scanning

The Dexa analyses are performed by the ultra high resolution PIXIMUS Series Densitometer (0.18×0.18 mm pixels, GE Medical Systems, Madison, Wis., USA). Bone mineral density (BMD in $g/cm^2$) and body composition are determined by using the PIXIMUS software (version 1.4×, GE Medical Systems).

D—Non-Invasive Blood Pressure Measurement and Pulse

The Visitech BP-2000 Blood Pressure Analysis System is a computer-automated tail'cuff system that is used for taking multiple measurements on 4 awake mice simultaneously without operator intervention. The mice are contained in individual dark chambers on a heated platform with their tails threaded through a tail cuff. The system measures blood pressure by determining the cuff pressure at which the blood flow to the tail is eliminated. A photoelectric sensor detects the specimen's pulse. The system generates results that have been shown to correspond closely with mean intra-arterial pressure measured simultaneously in the carotid artery. This allows reproducible values of systolic blood pressure and heart beat rate to be obtained. This requires training of the animals for one week in the system.

E—Circadian Activity

Spontaneous locomotor activity is measured using individual boxes, each composed with a sliding floor, a detachable cage, and equipped with infra-red captors allowing measurement of ambulatory locomotor activity and rears. Boxes are linked to a computer using an electronic interface (e.g., Imetronic, Pessac, France). Mice are tested for 32 hours in order to measure habituation to the apparatus as well as nocturnal and diurnal activities. The quantity of water consumed is measured during the test period using an automated lickometer.

Example 4

Physico-Chemical Properties

Water Solubility

Solid BAs were suspended in 5 ml of 0.1 M HCl. The saturated solutions, after incubation and gentle mixing for 1 week, were filtered on a Millipore filter (0.22 μpm) and the concentration of BA was measured by HPLC-ESI-MS/MS using C18 column (150 mm×2 mm i.d., 4 μm) and mobile phases of water containing 15 mM acetic acid pH 5 and acetonitrile. The flow rate was 150 μl/min. The mass spectrometry acquisition was performed in the multiple reaction monitoring mode using the ESI source in negative ionization. Water solubility was expressed as μmmol/liter.

The water solubility was measured for the insoluble protonated species of carboxylated bile acids at a pH 1. The water solubility of compound 10 was 120 μM (see Table 2).

The different position of one hydroxyl (16-position) in the compound 10 slightly reduced the solubility in respect to conventional 3,7,12 trihydroxy bile acid cholic acid. The water solubility increased by increasing the pH and at pH 7 compound 10 was highly water soluble. The data in Table 2 shows that the carboxylated analogue compound 10 when administered in its acid form remains insoluble in the gastric content at a low pH and goes into solution to form the salt (anion) once excreted into the duodenum due to the higher pH of the pancreatic and duodenal fluids. In bile, the compound remains in solution eventually forming micelles at high concentrations.

TABLE 2

| Bile Acid | Ws[a] (μM) | CMC[b] 0.15M Na+ (mM) | ST$_{CMC}$[c] Dyne/cm | LogP$_A$-[d] | Albumin Binding[e] (%) |
|---|---|---|---|---|---|
| CDCA | 32 | 3.2 | 45.5 | 2.2 | 93 |
| UDCA | 7.5 | 6.0 | 50.5 | 2.2 | 94 |
| CA | 273* | 11* | — | 1.1* | 50* |
| TCDCA | hs | 3.0* | — | 0.9* | 70* |
| TUDCA | hs | 2.2* | — | 1.1* | 67* |
| 6MUDCA | 28* | 4.2* | — | 1.3* | 80* |
| 10 | 120 | 5.9 | 52.4 | 1.6 | 83 |

[a]Ws: water solubility refers to BA as protonated species and therefore not evaluated for TCDCA and TUDCA which are highly soluble (hs).
[b]CMC: Critical Micellar Concentration determined in 0.15M NaCl water solution.
[c]ST$_{CMC}$: Surface Tension at CMC in 0.15M NaCl water solution.
[d]LogP$_A$: 1-octanol-water partition coefficient of the studied bile acids as ionized species.
*values from literature.

Critical Micellar Concentration (CMC)

The detergency i.e. the tendency to form micelles was evaluated for all the charged molecules which are soluble in water as Sodium salt (2 unit up the pKa). The critical micellar concentration (CMC) was determined by surface tension (ST) measurements using a maximum bubble-pressure method which give surface tension values slightly affected by potential impurities similar to static methods. The tensiometer was a Sensadyne 6000 (Chem-Dyne Research Corp., Milwaukee, Wis.) equipped with two glass probes of 0.5 and 4.0 mm diameters connected to a source of nitrogen. The bubble frequency was 1 bubble/second in distilled water at 26° C. (P=2.7 atm) and the calibration was made with double-distilled water and methanol. The surface tension of BA sodium salts solutions in NaCl 0.15 M was measured at various concentrations ranging from 0.10-50 mM range. The surface tension values were plotted against the logarithm of the bile salt concentration; the regression lines corresponding to the two parts of the curve (monomeric and micellar phases) were calculated using the method of least squares, and the intersection of the lines was taken as the CMC value. From the ST vs concentration curves the value of the surface tension at the CMC (equilibrium between monomers and multimers species) was also calculated giving information about the detergency power which is related to the size of the micelles with associate surface tension lowering capacity.

Figure 6:
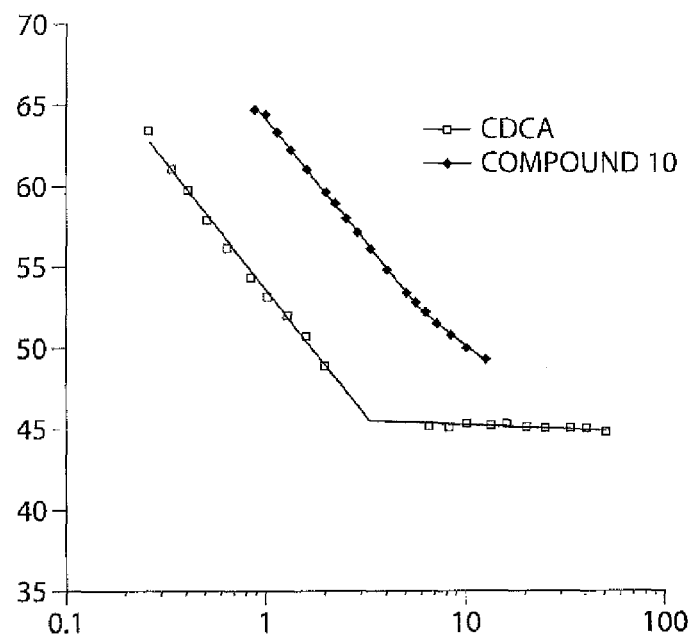
FIG. 6 is a graph that depicts the surface tension plotted against the logarithm of the concentration of compound 10 (mM) in NaCl 0.15M.

The CMC was evaluated by surface tension measurements in non equilibrium conditions i.e. in conditions that impurities slightly affect the surface tension results (FIG. 6). Table 2 shows the results. Compound 10 presented a high CMC with a low surface tension lowering capacity which indicated that this compound is a moderate detergent and the micelles have a very low aggregation number. The presence of a hydroxyl group in the C-16 beta position reduces the hydrophobic area responsible for back to back interaction, which is to form micelles and therefore, the micelles are small and poorly detergent. This property confers to the molecule a low toxicity when accumulated in a given biological fluid or organ.

Octanol/Water Partition Coefficient

The octanol/water partition coefficient was measured for molecules in their ionized form and therefore the carboxy analogues were studied at a relatively high pH (8 to 9) to ensure full ionization of the carboxyl group. The 1-Octanol/water partition coefficient (log P) was evaluated using a conventional shake-flask procedure. The experiments were carried out on 0.1 mM bile salt solution buffered at pH 8 with 0.1 M phosphate buffer to ensure complete ionization of the BA; the log P values refer to the BA in the ionized form, not to the protonated species, and the initial concentration of each BA was below its own CMC value. The aqueous buffer was previously pre-saturated with 1-octanol, 5 ml of 1-octanol pre-saturated with water was then added and the samples were left to equilibrate for 2 weeks under continuous stirring at room temperature. After centrifugation the two phases were carefully separated. BA concentration in the water phase was measured with HPLC-ESI¬MS/MS using a C18 column (150 mm×2 mm i.d., 4 μm) and with water containing 15 mM acetic acid pH 5 and acetonitrile for mobile phases. The flow rate was 150 μal/min and the column was maintained at 45° C. The mass spectrometry acquisition was performed in the multiple reaction monitoring mode using the ESI source in negative ionization.

Table 2 shows the results. The carboxylated compound 10 with three hydroxyl groups in 3α, 7α and 16β positions presented a slightly higher lipophilicity in respect to the natural, analogue CA due to the presence of the ethyl in C-6 position. The difference is likely due to the uncommon position of the 16-beta hydroxyl group, considering that the 12-alpha position does not appear to play a major role in the detergency properties.

Albumin Binding

The extent of albumin binding was evaluated by equilibrium dialysis at a fixed BA-albumin ratio. Each BA was dissolved at a concentration of 100 μM in 5% bovine serum albumin-saline solution (pH 7.2) and left to stand for 24 h at 25° C. Two milliliters of this solution was dialyzed in cellulose sacs having a molecular weight cut-off of 12,000-14,000 Dalton against 25 ml of saline solution. The system was equilibrated by gently shaking for 72 h at 25° C. BA concentrations of the dialyzed solution (corresponding to the free unbound fraction) and of the starting solution were determined with HPLC-ESI-MS/MS in the same conditions of the previous analysis.

The percentage of albumin binding was calculated from the initial BA concentration and from the unbound concentration in the dialyzed fraction. Data are reported in the Table 2.

The percent binding of compound 10 is higher than CA as a result of the methyl group in the side chain. Compound 10 presents an albumin binding compatible with a relatively fast hepatic uptake, similar to natural occurring BA.

Example 5

In Vitro Metabolic Stability in Human Stools Culture

Stability to Intestinal Bacteria.
7α-dehydroxylation.

Homogenized fresh human stools (500 mg) were transferred into sterile vials to which 5 mL of sterilized chopped meat-glucose medium (Scott Lab., Fiskville, R.I.) was added. BAs were then added at a final concentration of 0.05 mM. Vials were incubated at 37° C.; then, at 0, 1, 2, 4, 8 and 24 h after the addition of the BA, the reaction was stopped with 150 µL of 30% KOH. The samples were centrifuged at 3500 rpm for 10 min; from the supernatant the BA were isolated by C-18 solid-phase extraction and analyzed by TLC and HPLC-ES-MS/MS.

Thin-layer chromatography (TLC), utilizing silica gel 0.25 mm thickness plates (Merck, Darmstat, Germany), was employed as the first screening test. The solvent system used for the separation of conjugated BA was composed of propionic acid/isoamyl acetate/water/N-propanol (3:4:1:2, v/v/v/v; solvent I), and that of the unconjugated BA was acetic acid/carbon tetrachloride/isopropyl ether/isoamyl acetate/water/N-propanol/benzene (1:4:6:8:2:2, v/v/v/v/v; solvent II). Separated BA were revealed with 5% phosphomolybdic acid ethanol solution.

Compound 10 was very stable when incubated in human stool cultures and, even after 24 hour, more than 85% of the compound was recovered unmodified. On the contrary the reference, natural analogue chenodeoxycholic (CDCA) presented a half-life time of almost one hour and after 8 hours of incubation was almost completely metabolized (7-dehydroxylated) to form lithocholic acid. Also, after a long time incubation, the 7 dehydroxylation and the intermediate formation of a 7 oxo derivative was practically abolished.

Side Chain Stability

According to the first results, the side chain was not modified by the intestinal bacteria enzymatic activities. These data suggest that the presence of the ethyl group in the C-6 position protects the 7-hydroxyl group toward oxidation or removal by steric hindrance. In addition compound 10 is also very stable for side chain metabolism.

Example 6

Biliary Secretion and Metabolism of Compound 10 in Bile-Fistula Rat after Duodenal (id) and Femoral (iv) Administration Aim and Rationale The structural modification of the new BA analogues could affect their hepatic uptake, hepatic transports and secretion and intestinal absorption. Therefore, the knowledge of the biliary secretion after either iv and id administration together their metabolism is a key point in the candidate selection for additional studies.

To evaluate the mode and efficiency of the intestinal absorption, compound 10 was administered both intravenously (femoral infusion) and orally (duodenal infusion) at the same dose and its biliary secretion rate was evaluated in bile fistula rat model. The choleretic effect on bile production was also evaluated. The differences in the area under the curve (AUC) of the biliary secretion vs time between iv and id administration account of its intestinal absorption and give information about its bioavailability. Moreover, the hepatic and intestinal metabolism could also be quite different and therefore the biliary secretion of compound 10 and its main (intestinal) and hepatic metabolites were determined.

Choleretic Effect

Duodenal Infusion

The bile fistula rat model was developed at the University of Bologna Lab facilities. The compounds were administered at a dose of 1 µmol/kg/min (1 hour infusion) to a rat group via duodenal infusion (id). The rats have a bile fistula to collect bile samples at different times before and during the infusion. For duodenal infusion experiment, 6 rats (250±10 g) were treated. Bile samples were collected every 15 minutes for four hours. In addition, 3 control rats were treated with saline solution under the same conditions for times and sampling (duodenal control rats).

Figure 7:
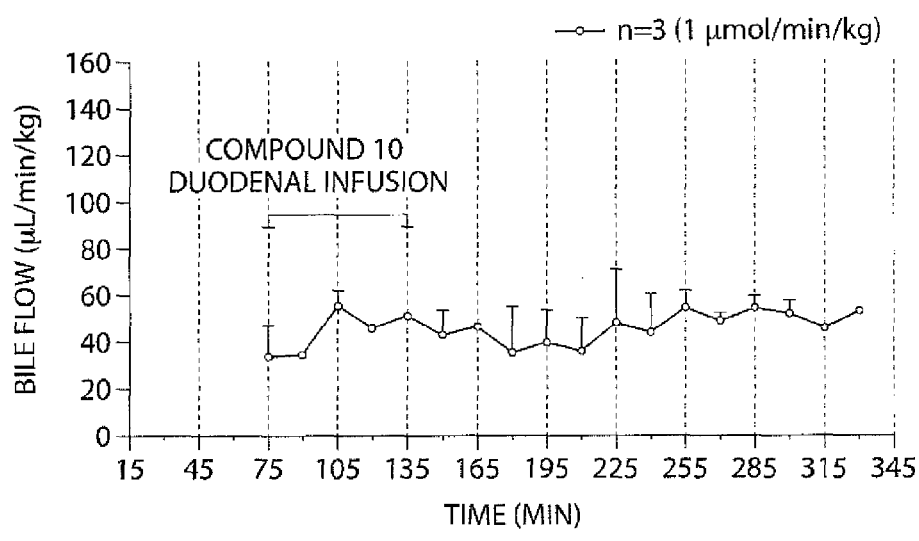
FIG. 7 is a bile flow chart for a duodenal infusion experiment performed using compound 10.

FIG. 7 shows bile flow during sample collection (one animal). Duodenal infusion starts after 30 min baseline bile collection and continues for one hour. Compound 10 is not choleretic and the bile flow is similar to control group.

Intravenous Infusion

Figure 8:
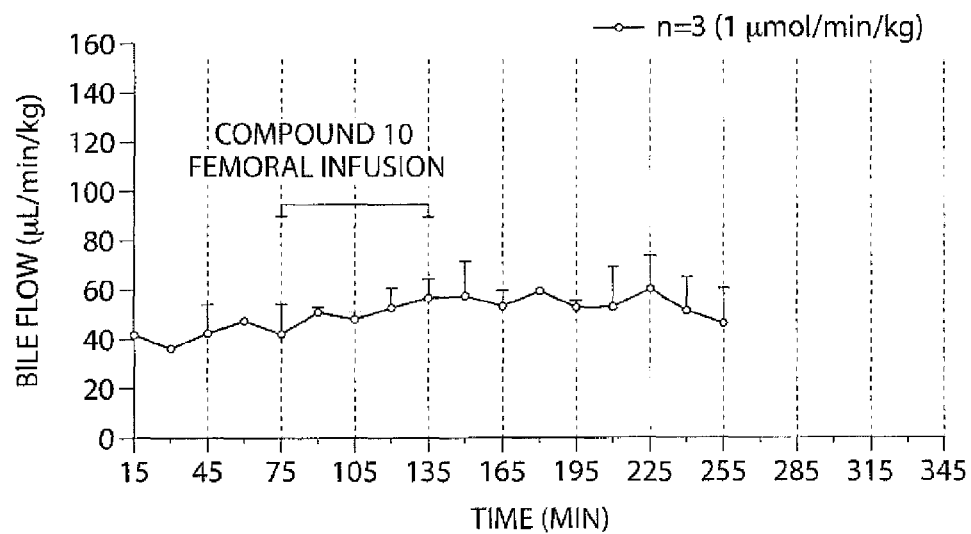
FIG. 8 is a bile flow chart for a femoral infusion experiment performed using compound 10.

For femoral infusion experiment, 6 rats (body weight, 250±10 g) were treated with compound 10 at 1 µmol/min/kg. FIG. 8 shows bile flow during the study. Femoral infusion starts after 75 minutes of steady-state and continues for 60 min. Bile samples were collected every 15 minutes for four hours. In addition, 3 rats were treated with saline solution under the same conditions for times and sampling (femoral control rats).

The bile flow during iv infusion of 3% BSA Saline vehicle (control, n=1) maintained a value ranging from 40 to 80 µL/min/kg for the entire period of the experiment. FIG. 8 reports the bile flow after iv infusion of CDCA as the reference compound. No significant differences with respect to the control experiment were observed and the maximum flow rate was just slightly higher than the control case (80 versus 70 µL/min/kg)

Biliary Secretion of the Administered Analogues

Bile samples collected during the iv and id experiments were analyzed to determine the biliary secretion of the administered analogues and their metabolites. HPLC-ES-MS/MS analysis. Pure crystalline powder of each compound was obtained from the R. Pellicciari laboratory of Perugia. Stock solutions in methanol at 1 mmol/L (with the exception of compound 10 at 350 µmol/L) was prepared and working solutions were prepared by diluting appropriate volumes of the primary solution. Methanol and acetonitrile was of HPLC-grade purity. Ammonia was 30% and acetic acid was 99.8%. All reagents were obtained from Carlo Erba Reagents. HPLC-grade water was prepared by a Milli-Q system.

Sample Preparation

Rat bile samples were brought to room temperature, briefly stirred, and diluted 1:100 v/v (bile samples from duodenal orinfusion) and 1:100 or 1:200 v/v (bile samples from femoralr infusion) with 15 mM ammonium acetate buffer (pH=5.0):acetonitrile=70:30 (v/v). Final solution was transferred in autosampler vials, and 10 μL was injected into the chromatographic column.

HPLC-ESI-MS/MS Method

Bile rat samples were analyzed by liquid chromatography-tandem mass spectrometry (HPLC-MS/MS) using electrospray (ESI) source in negative ionization mode. For liquid chromatography a Waters Alliance 2695 separation module coupled with autosampler was used. Autosampler was maintained at 7° C. Separation was performed on a Synergi Hydro-RP $C_{18}$ column (150×2.0 mm i.d., 4 μm particle size), protected by a SecurityGuard ODS 4×2.0 mm i.d. precolumn, both supplied from Phenomenex. Analyte was eluted using 15 mM ammonium acetate buffer (pH=5.00) as mobile phase A and acetonitrile as mobile phase B. Mobile phase B was increased from 30% to 64% in 10 min, then to 100% in 10 min, and held constant for 10 min. Flow rate was 150 μL/min and the column was maintained at 45° C. The column effluent was introduced into ESI source connected to a triple quadruple mass spectrometer (Quattro-LC, Micromass) operating in Multiple Reaction Monitoring (MRM) acquisition mode. Nitrogen was used as nebulizer gas at 90 L/h flow rate and as desolvation gas at 930 L/h. Ion source block and desolvation temperatures were set respectively to 80° C. and 180° C. Capillary voltage was 3.0 kV.

MassLynx software version 4.0 was used for data acquisition and processing. In addition, using mass spectrometry both in single MS or tandem MS/MS configuration experiments were performed to identify metabolites.

Quantification

A 5-point calibration curve was daily prepared and injected in duplicate. Calibration samples were obtained in the 0.1 to 25 μmol/L concentration range prepared in mobile phase. Linear calibration curve parameters were obtained from the plot of the analyte peak area versus analyte concentration using a least squares regression analysis (weight=$1/x^2$). Correlation coefficients were ≥0.989.

Pharmacokinetic (Biliary Secretion) of the Administered Analogues: iv Versus id Comparison The data refer to the secretion rate of the analogues recovered in bile as such after duodenal and femoral infusion at a dose of 1 μmol/Kg/min. Major and minor metabolites are reported later.

Table 3 shows concentration and secretion values for compound 10 obtained from bile rat samples collected during the duodenal infusion (1 h ranging from 75 to 135 min).

TABLE 3

| Time (min) | Conc. (mmol/L) | Secretion (μmol/kg/min) |
|---|---|---|
| 90 | 0.01 | 0.0004 |
| 120 | 0.07 | 0.003 |
| 150 | 0.39 | 0.019 |
| 180 | 0.14 | 0.003 |
| 210 | 0.09 | 0.004 |
| 240 | 0.03 | 0.001 |
| 270 | 0.02 | 0.001 |
| 300 | 0.02 | 0.001 |

Table 4 shows concentration and secretion values for compound 10 obtained from bile rat samples collected during the femoral infusion (1 h ranging from 75 to 135 min).

TABLE 4

| Time (min) | Conc. (mmol/L) | Secretion (μmol/kg/min) |
|---|---|---|
| 75 | 0.04 | 0.002 |
| 90 | 2.3 | 0.127 |
| 120 | 0.90 | 0.065 |
| 150 | 0.06 | 0.004 |
| 180 | 0.04 | 0.003 |
| 210 | 0.02 | 0.001 |
| 240 | n.d.[b] | —[a] |

[a]—: not calculated
[b]n.d.: not detected

Figure 9:
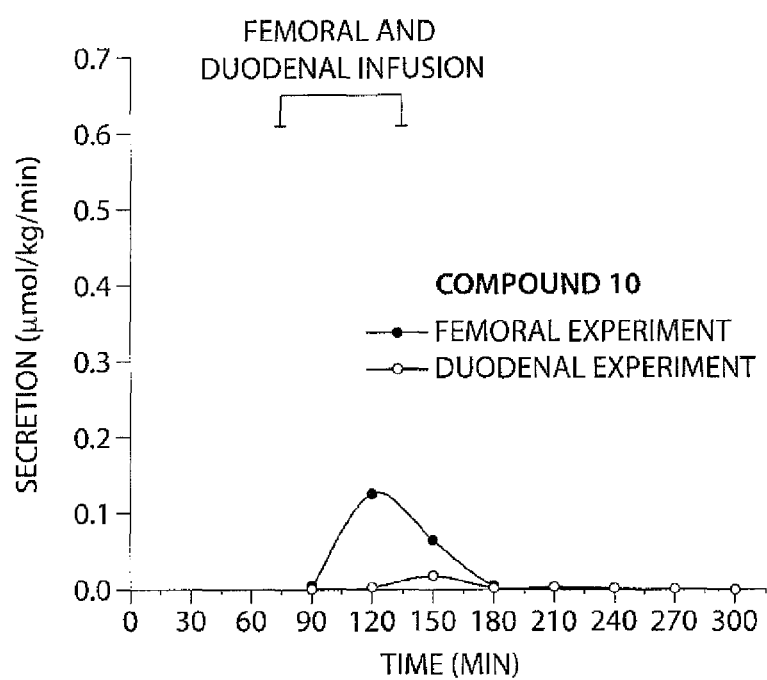
FIG. 9 is a graph that depicts secretion rates versus time in femoral and duodenal infusion experiments performed using compound 10.

The biliary secretion of compound 10 after iv infusion is not efficient and the maximum secretion rate inlow (FIG. 9). The compound is metabolized to form the taurine conjugate and this contributes to slightly improve its recovery. The biliary secretion after id administration is much less than the iv experiments suggesting a poor intestinal absorption of the molecule.

Hepatic Metabolism

Figure 10A:
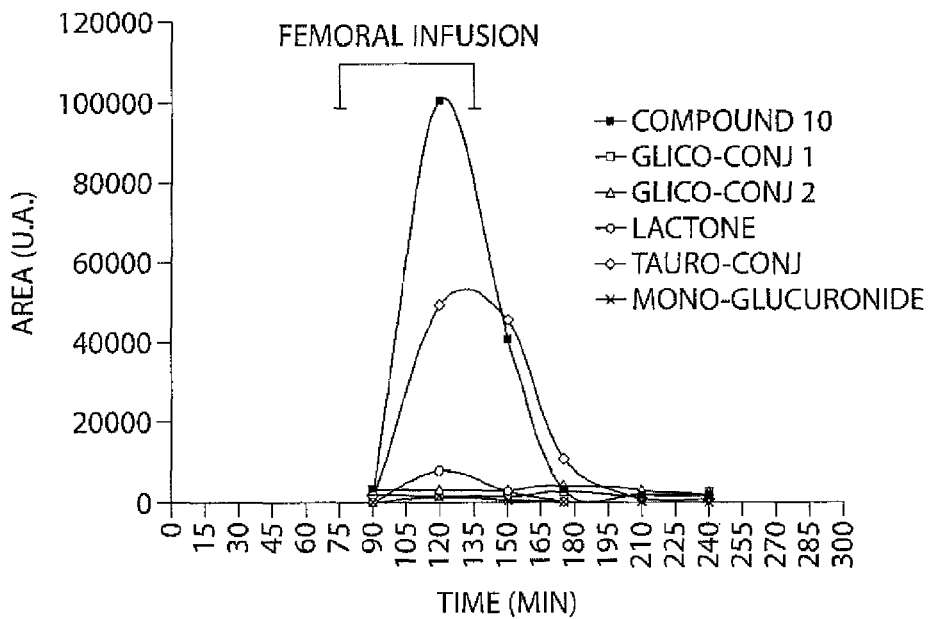
FIG. 10 is a series of graphs that shows compound 10 and its main metabolite identified in bile using mass spectrometry in an iv experiment. Data are reported as absolute area values.

Compound 10 undergoes to an hepatic metabolism like natural occurring BA. After iv administration is secreted in bile as such and mainly conjugated with taurine Minor metabolites such as lactone and a monoglucuronide metabolites has been also found. After id administration the molecule is recovered as such and mainly metabolised to form the taurine conjugates. FIG. 10a: Compound 10 and its main metabolites identified in bile using mass spectrometry in the iv experiment. Data are reported as absolute area values.

Figure 10B:
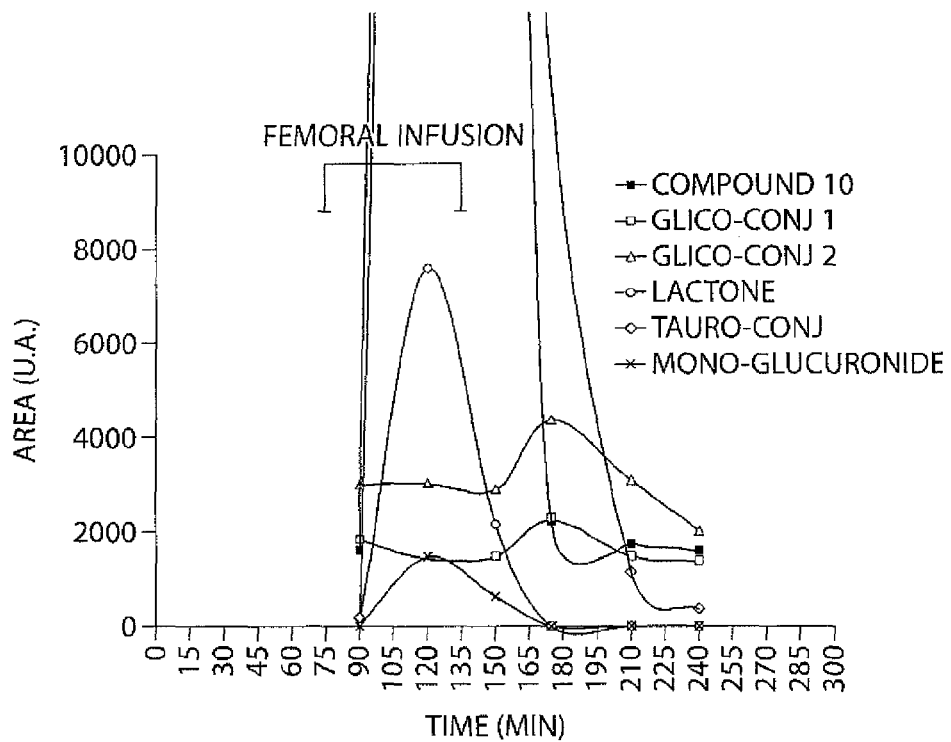

FIG. 10b: Zoom display of FIG. 10a.

Figure 10C:
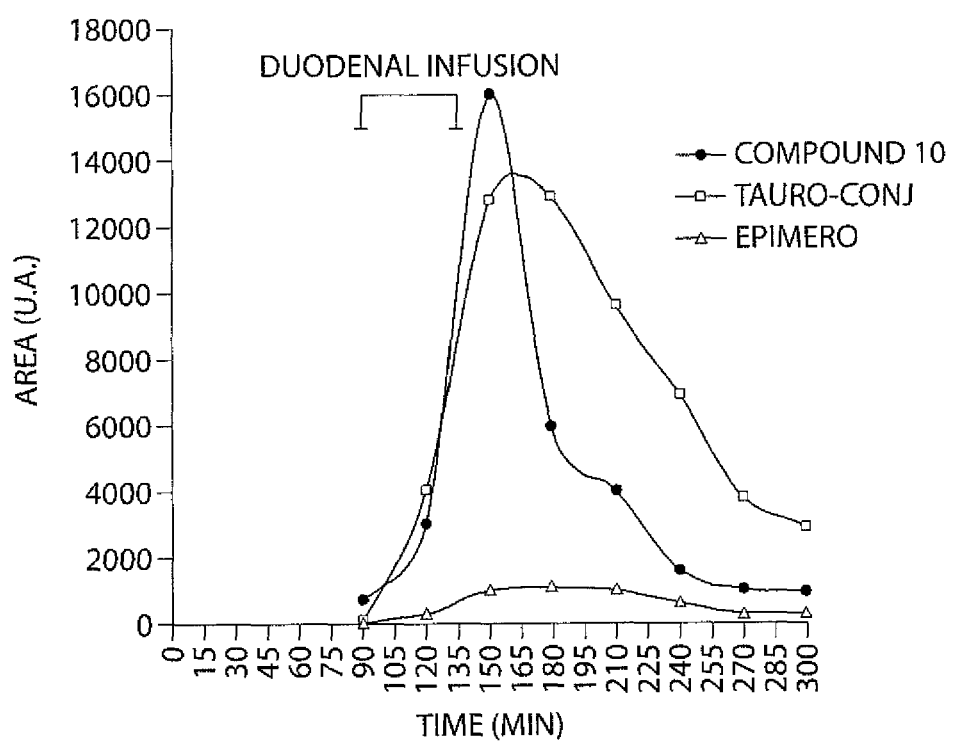

FIG. 10c: Compound 10 and its main metabolites identified in bile using mass spectrometry in the di experiment. Data are reported as absolute area values.

Compound 10 is moderately hydrophilic with a low detergency. The hepatic uptake is efficient and also the intestinal absorption. The compound is secreted in bile as such and mainly as taurine conjugate and the recovery in bile almost complete.

Example 7

In Vitro Toxicity on HepG2 Cell

Compounds of the invention were evaluated for in vitro toxicity using a HepG2 cell assay. HepG2 cell cytotoxicity was determined by monitoring ATP decrease and HepG2 cell apotosis was determined by monitoring caspase-3 activation. The results are shown in Table 5.

Cytotoxicity

Cell viability was measured using Perkinelmer ATP-Lite 1 STEP. ATP is a marker for cell viability because it is present in all metabolically active cells and the concentration declines very rapidly when the cells undergo necrosis or apoptosis. Human NCI-H716 or HepG2 cells ($1 \times 10^4$) were seeded in 96 wells plate and stimulated with 10-fold dilutions from 1 nM to 300 μM of the compound 10 for 4 h at 37° C. The plates were equilibrate at RT for 10 minutes and 100 μl of ATP-Lite 1 STEP Reagent was added to 100 μl of culture medium containing cells. Luminescence was read with Victor Light (PerkinElemr). The experimental signal was subtracted from background. Tamoxifen was used as positive control of cellular cytotoxicity, while negative control was the non treated cells.

Apoptosis

Caspases participate in the molecular control of apoptosis and TruPoint Caspase-3 Substrate enables sensitive, robust and homogeneous time-resolved fluorescence assay of caspase-3 activity.

Human Hepatocytes cells (HepG2) were seeded ($1 \times 10^4$) in 96 well plate with HepG2 medium without sodium pyruvate. The cells were stimulated 4 h at 37° C. with serial dilutions of test compound from 1 nM to 300 µM in triplicate. Staurosporin was used as positive control of apoptotic cells. Negative controls were: 1. Unstimulated cells; 2. Medium alone without cells; 3. Cells incubated without the caspase substrate. Lyses buffer and Caspase-3 Substrate were added to the cells and 1 hour and 24 hours after fluorescence was measured with EnVision.

Necrosis

The cellular necrosis was analyzed by measuring the release of Lactato DeHydroxegenase (LDH) from the necrotic cells using Promega's CytoTox ONE Homogeneous Membrane Integrity Assay. Human hepatocyte cells ($1 \times 10^4$) were seeded in a 96 well plate. After 18 hours of incubation fresh medium without Sodium Pyruvate and Serum free was replaced and compound 10 were added in dose response from 0.1 µM to 500 µM. Triton 1% was used as maximum LDH release control. Tamoxifen was used as inducer necrosis. The plated cells were placed back into the incubator for an additional 4 hours. The supernatant was transferred in a new plate and the same volume of CytoTox-ONE Reagent was added to the plate. After 1 h of incubation the fluorescence was read with the EnVision multilabel plate reader with an excitation wavelength of 560 nm and an emission of 590 nm.

TABLE 5

In Vitro Toxicity on HepG2 cells

| Compound | CYTOTOXICITY ATP decrease $EC_{50}$ (µM) | APOPTOSIS Caspase-3 activation $EC_{50}$ (µM) | NECROSIS LDH release $EC_{50}$ (µM) |
|---|---|---|---|
| Staurosporine (apoptosis) | 15 | 3 | n.d. |
| Tamoxifen (Necrosis) | 47 | 4 | 35 |
| LCA | 84 | 65 | 105 |

TABLE 5-continued

In Vitro Toxicity on HepG2 cells

| Compound | CYTOTOXICITY ATP decrease $EC_{50}$ (µM) | APOPTOSIS Caspase-3 activation $EC_{50}$ (µM) | NECROSIS LDH release $EC_{50}$ (µM) |
|---|---|---|---|
| CDCA | 650 | 890 | >1000 |
| UDCA | >1000 | n.d. | n.d. |
| CA | >1000 | n.d. | n.d. |
| Compound 10 | >1000 | n.d. | n.d. | n.d., Not Detected

Example 8

NR Selectivity Assays

The selectivity of compounds of the invention was evaluated using assay methods known in the art. Specifically, the following assay methods were used:
FXR and LXR: Coactivator Recruitment (alphascreen);
TGR5: cAMP level on human intestinal cell line (NCI-H716);
PXR: Ligands Competition assay (Binding Assay)
CAR: Coactivator Recruitment (Lanthascreen)
Table 6 shows the results of these assays.
TR-FRET Coactivator Assay Lanthascreen assay (Invitrogen) was used for nuclear receptor selectivity assay. The kit uses a terbium-labeled anti-GST antibody, a fluorescein-labeled coactivator peptide, and a NR ligand-binding domain that is tagged with glutathione-S-transferase (GST) in a homogenous mix-and-read assay format. The assays were performed in 384 microwell plate (PerkinElmer). A 20 µl total assay reaction included 5 nM GST-tagged NRs, 125 nM of coregulator peptide, 5 nM of TB-anti-GST tagged antibody (terbium-anti-glutathione S transferase tagged), 5 mM DTT and varying concentration of compound 10 in the assay buffer supplied by Invitrogen. The negative control was devoid of the compound 10 but contained everything else contained in the agonist well. Following 1 hour incubation in the dark, TR-FRET measurements were made in the Envision. The emission ratio 520/495 was plotted against varying ligand concentrations. The data was analyzed using GraphPad Prism using the sigmoidal curve equation with variable slope to obtain $EC_{50}$ values.

TABLE 6

NR Selectivity Assays

| Compound (Reference Standard) | FXR Activation (CDCA = 10-20 µM) $EC_{50}$ (µM) | TGR5 Activation (LCA = 4-8 µM) $EC_{50}$ (µM) | LXRα Activation (T0901317 = 0.08 µM) $EC_{50}$ (µM) | PXR Binding (SR-12183 = 0.013 µM) $IC_{50}$ (µM) | CAR Activation (CITCO = 0.005 µM) $EC_{50}$ (µM) | PPARδ Activation (GW0742 = 0.004 µM) $EC_{50}$ (µM) | VDR Activation (Di-HydroxyVitD3 = 0.005 µM) $EC_{50}$ (µM) |
|---|---|---|---|---|---|---|---|
| CDCA | 20 | 30 | No activity | >250 | >250* | No activity | No activity |
| LCA | No activity | 4-8 | No activity | 23 | No activity | No activity | No activity |
| CA | No activity | 30 | No activity | No activity | No activity | No activity | No activity |
| UDCA | >150 | No activity | No activity | >250 | >250* | No activity | No activity |
| Compound 10 | 12 | 0.6 | No activity | 64 | No activity | No activity | No activity |

Assay Methods

FXR and LXR: Coactivator Recruitment (Alphascreen);

TGR-5: cAMP level on human intestinal cell line (NCI-H716);

PXR: Ligands Competition assay (Binding Assay);

*: data representing inverse agonism

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed:

1. A compound of formula A:

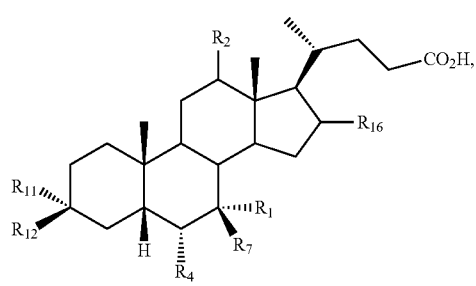

(A)

or a salt, solvate, hydrate, or amino acid conjugate thereof, wherein:

$R_1$ is hydrogen, hydroxyl, substituted or unsubstituted alkyl, or halogen;

$R_2$ is hydrogen or hydroxyl;

$R_4$ is substituted or unsubstituted alkyl or halogen;

$R_7$ is hydrogen, substituted or unsubstituted alkyl, or hydroxyl;

$R_{11}$ is hydroxyl, $OSO_3H$, $OSO_3^-$, $OCOCH_3$, $OPO_3H$, $OPO_3^{2-}$, $OC_6H_8O_6^-$, or hydrogen;

$R_{12}$ is hydroxyl, $OSO_3H$, $OSO_3^-$, $OCOCH_3$, $OPO_3H$, $OPO_3^{2-}$, $OC_6H_8O_6^-$, or hydrogen, or taken together $R_{11}$ and $R_{12}$ form a carbonyl; and $R_{16}$ is hydroxyl, alkoxy, or halogen.

2. The compound of claim 1, wherein the compound is of formula B:

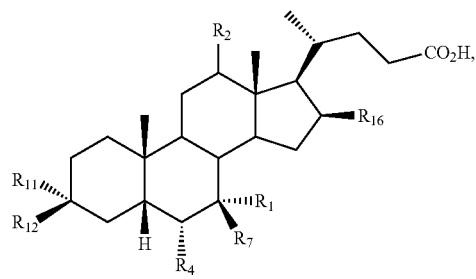

(B)

or a salt, solvate, hydrate, or amino acid conjugate thereof.

3. The compound of claim 1, wherein the compound is of formula C:

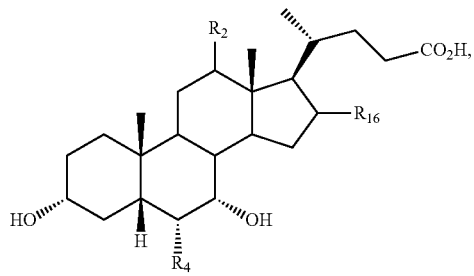

(C)

or a salt, solvate, hydrate, or amino acid conjugate thereof.

4. The compound of claim 2, wherein the compound is of formula D:

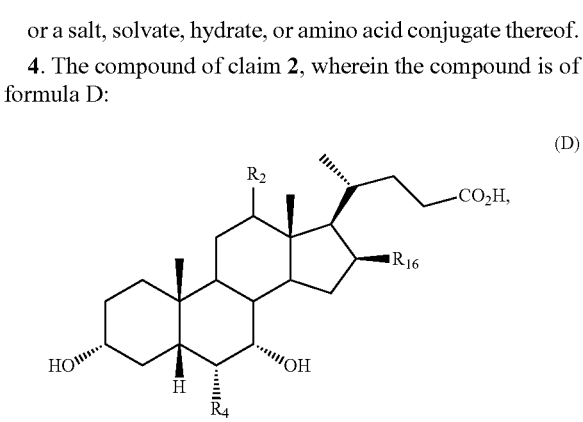

(D)

or a salt, solvate, hydrate, or amino acid conjugate thereof.

5. The compound of claim 1, wherein the compound is of formula E:

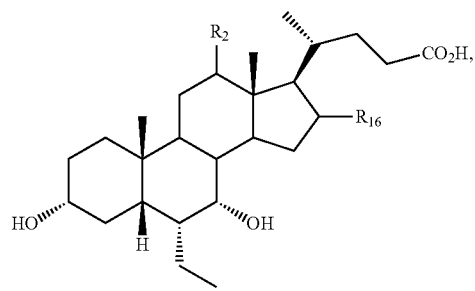

(E)

or a salt, solvate, hydrate, or amino acid conjugate thereof.

6. The compound of claim 5, wherein the compound is of formula F:

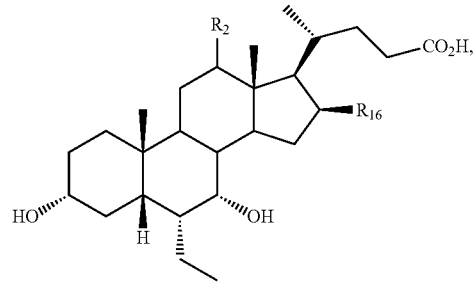

(F)

or a salt, solvate, hydrate, or amino acid conjugate thereof.

7. A compound, wherein the compound is Compound 10:

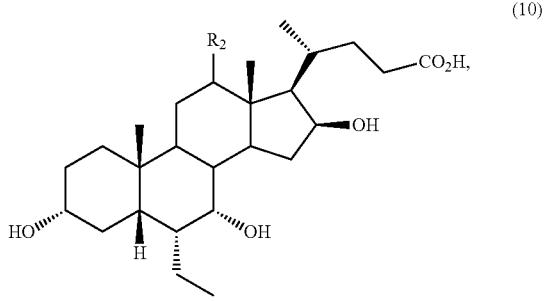

(10)

or a salt, solvate, hydrate, or amino acid conjugate thereof.

8. The compound of claim 7, wherein the compound is a pharmaceutically acceptable salt.

9. The compound of claim 1, wherein the compound is a pharmaceutically acceptable salt.

10. A pharmaceutical composition comprising a compound of claim 1 or a salt, solvate, hydrate, or amino acid conjugate thereof and at least one pharmaceutically acceptable excipient.

11. A method of ameliorating a disease selected from obesity, diabetes, metabolic syndrome, insulin resistance, hypertension, and dyslipidemia, comprising administering the compound of claim 1 or a salt, solvate, hydrate, or amino acid conjugate thereof to a subject in need thereof.

12. The method of claim 1, wherein the compound or a salt, solvate, hydrate, or amino acid conjugate thereof is administered to a subject orally, parentally, intravenously, or topically.

13. The method of claim 11, wherein the subject is a human.

14. A pharmaceutical composition comprising a compound of claim 7 or a salt, solvate, hydrate, or amino acid conjugate thereof and at least one pharmaceutically acceptable excipient.

15. A method of ameliorating a disease selected from obesity, diabetes, metabolic syndrome, insulin resistance, hypertension, and dyslipidemia, comprising administering the compound of claim 7 or a salt, solvate, hydrate, or amino acid conjugate thereof to a subject in need thereof.

16. The method of claim 15, wherein the compound or a salt, solvate, hydrate, or amino acid conjugate thereof is administered to a subject orally, parentally, intravenously, or topically.

17. The method of claim 15, wherein the subject is a human.

* * * * *